United States Patent [19]

Hewawasam et al.

[11] Patent Number: 5,602,169
[45] Date of Patent: Feb. 11, 1997

[54] 3-SUBSTITUTED OXINDOLE DERIVATIVES AS POTASSIUM CHANNEL MODULATORS

[75] Inventors: Piyasena Hewawasam, Middletown; Nicholas A. Meanwell, East Hampton; Valentin K. Gribkoff, Wallingford, all of Conn.

[73] Assignee: Bristol-Myers Squibb Company, Princeton, N.J.

[21] Appl. No.: 635,316

[22] Filed: Apr. 19, 1996

Related U.S. Application Data

[63] Continuation-in-part of Ser. No. 477,047, Jun. 7, 1995.
[51] Int. Cl.$^6$ .................... A61K 31/40; C07D 209/12
[52] U.S. Cl. ............................... 514/418; 548/486
[58] Field of Search .................. 514/418; 548/486

[56] References Cited

U.S. PATENT DOCUMENTS

| | | | |
|---|---|---|---|
| 4,542,148 | 9/1985 | Kuch et al. | 514/418 |
| 4,614,739 | 9/1986 | Kuch et al. | 514/212 |
| 5,200,422 | 4/1993 | Olesen et al. | 514/387 |
| 5,373,019 | 12/1994 | Zilch et al. | 514/423 |

FOREIGN PATENT DOCUMENTS

| | | |
|---|---|---|
| 477819 | 1/1992 | European Pat. Off. . |
| WO93/08800 | 5/1993 | WIPO . |
| WO95/18105 | 7/1995 | WIPO . |

OTHER PUBLICATIONS

Cook, N. S. *Trends in Pharmacol. Sciences* (1988), 9, 21.
Singer, J. et al., *Pflugers Archiv.* (1987) 408, 98.
Baro, I., et al., *Pflugers Archiv.* (1989) 414 (Suppl. 1), S168.
Laurent, F. et al., *Br. J. Pharmacol.* 1993 108, 622–626.
Koh, D-S., et al., *Neuroscience Lett.* (1994) 165, 167–170.
Olesen, et al., *European J. Pharmacol.*, 251, 53–59 (1994).
Quast, U., et al., *Trends in Pharmacol Sciences* (1989) 10, 431.
Ahmed, F., et al., *Br. J. Pharmacol* (1984) 83, 227.

Primary Examiner—Joseph McKane
Attorney, Agent, or Firm—Aldo A. Algieri

[57] ABSTRACT

There is provided novel substituted 3-phenyl oxindole derivatives of the formula

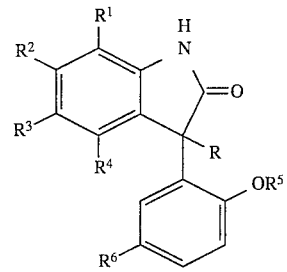

wherein
  R is hydrogen, hydroxy or fluoro;
  $R^1$, $R^2$, $R^3$ and $R^4$ each are independently hydrogen, $C_{1-4}$ alkyl, halogen, trifluoromethyl, phenyl, p-methylphenyl or p-trifluoromethylphenyl; or $R^1$ and $R^2$, $R^2$ and $R^3$ or $R^3$ and $R^4$ are joined together to form a benzo fused ring;
  $R^5$ is hydrogen or $C_{1-4}$ alkyl; and
  $R^6$ is chlorine or trifluoromethyl; or a nontoxic pharmaceutically acceptable salt, solvate or hydrate thereof, which are openers of the large-conductance calcium-activated potassium channels and are useful in the treatment of disorders which are responsive to the opening of the potassium channels.

10 Claims, No Drawings

3-SUBSTITUTED OXINDOLE DERIVATIVES AS POTASSIUM CHANNEL MODULATORS

CROSS-REFERENCE TO RELATED APPLICATION

This application is a continuation-in-part application of U.S. Ser. No. 08/477,047, filed Jun. 7, 1995, now pending which is herein incorporated by reference in its entirety.

FIELD OF THE INVENTION

The present invention is directed to novel substituted 3-phenyl oxindole derivatives which are modulators of the large-conductance calcium-activated potassium (Maxi-K) channels and, therefore, useful in the protection of neuronal cells, especially in the treatment or prevention of ischemic stroke. The present invention also provides a method of treatment with the novel oxindole derivatives and to pharmaceutical compositions thereof.

BACKGROUND OF THE INVENTION

Potassium channels play a key role in regulation of cell membrane potential and modulation of cell excitability. Potassium channels are largely regulated by voltage, cell metabolism, calcium and receptor mediated processes. [Cook, N. S., *Trends in Pharmacol. Sciences* (1988), 9, 21; and Quast, U., et al, *Trends in Pharmacol. Sciences* (1989), 10, 431]. Calcium-activated potassium ($K_{Ca}$) channels are a diverse group of ion channels that share a dependence on intracellular calcium ions for activity. The activity of $K_{Ca}$ channels is regulated by intracellular [$Ca^{2+}$], membrane potential and phosphorylation. On the basis of their single-channel conductances in symmetrical $K^+$ solutions, $K_{Ca}$ channels are divided into three subclasses: large conductance (maxi-K)>150 pS; intermediate conductance 50–150 pS; small conductance<50 pS. Large-conductance calcium-activated potassium (Maxi-K) channels are present in many excitable cells including neurons, cardiac cells and various types of smooth muscle cells. [Singer, J. et al., *Pflugers Archiv.* (1987) 408, 98; Baro, I., et al., *Pflugers Archiv.* (1989) 414 (Suppl. 1), S168; and Ahmed, F. et al., *Br. J. Pharmacol.* (1984) 83,227].

Potassium ions play a dominant role in controlling the resting membrane potential in most excitable cells and maintain the transmembrane voltage near the $K^+$ equilibrium potential ($E_k$) of about −90 mV. It has been shown that opening of potassium channels shift the cell membrane potential towards the equilibrium potassium membrane potential ($E_k$), resulting in hyperpolarization of the cell. [Cook, N. S., *Trends in Pharmacol. Sciences* (1988), 9, 21]. Hyperpolarized cells show a reduced response to potentially damaging depolarizing stimuli. Maxi-K channels which are regulated by both voltage and intracellular $Ca^{2+}$ act to limit depolarization and calcium entry and may be particularly effective in blocking damaging stimuli. Therefore cell hyperpolarization via opening of Maxi-K channels may result in protection of neuronal cells under ischemic conditions.

A range of synthetic and naturally occuring compounds with maxi-K opening activity have been reported. The avena pyrone extracted from *avena sativa*-common oats has been identified as a maxi-K channel opener using lipid bi-layer technique [International Patent application WO 93/08800, published May 13, 1993]. 6-Bromo-8-(methylamino)imidazo[1,2-a]pyrazine-2-carbonitrile (SCA-40) has been described as a maxi-K channel opener with very limited electrophysiological experiments [Laurent, F. et al., *Br. J. Pharmacol.* (1993) 108, 622–626]. The flavanoid, Phloretin has been found to increase the open probability of $Ca^{2+}$-activated potassium channels in myelinated nerve fibers of *Xenopus laevis* using outside-out patches [Koh, D-S., et al., *Neuroscience Lett.* (1994) 165, 167–170].

A number of substituted oxindoles have been disclosed as neuroanabolic agents by H. Kuch et al in U.S. Pat. Nos. 4,542,148, issued Sep. 17, 1985 and 4,614,739, issued Sep. 30, 1986.

In European patent application EP-477,819 published Jan. 4, 1992 and corresponding U.S. Pat. No. 5,200,422, issued Apr. 6, 1993 to Olesen, et al., a number of benzimidazole derivatives were disclosed as openers of maxi-K channels by using single-channel and whole-cell patch-clamp experiments in aortic smooth muscle cells. Further work was reported by Olesen, et al in *European J. Pharmacol.*, 251, 53–59 (1994).

Stroke is presently recognized as the third leading cause of adult disability and death in the United States and Europe. In the past decade, several therapeutic approaches for the minimization of stroke-related brain damage have been pursued including inhibitors of AMPA/kainate, N-methyl-D-aspartate (NMDA) and adenosine reuptake inhibitors. It is the object of the present invention to provide novel compounds that will modulate potassium channels, in particular, large-conductance calcium-activated potassium (Maxi-K) channels which will be useful in reducing neuronal damage during ischemic stroke.

SUMMARY OF THE INVENTION

The present invention provides novel oxindole derivatives having the general formula

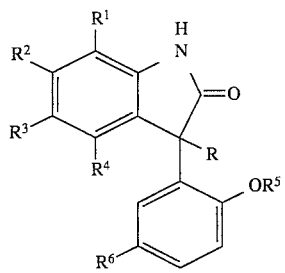

wherein R, $R^1$, $R^2$, $R^3$, $R^4$, $R^5$ and $R^6$ are as defined below, or a non-toxic pharmaceutically acceptable salt, solvate or hydrate thereof which are openers of the large conductance calcium-activated $K^+$ channels also known as maxi-K or BK channels. The present invention also provides pharmaceutical compositions comprising said oxindole derivatives and to the method of treatment of disorders sensitive to potassium channel opening activity such as ischemia, convulsions, asthma, urinary incontinence and traumatic brain injury.

DETAILED DESCRIPTION OF THE INVENTION

The present invention provides novel oxindole derivatives which are potent openers of the high conductance, calcium-activated K+-channels (BK channel) and which have the formula

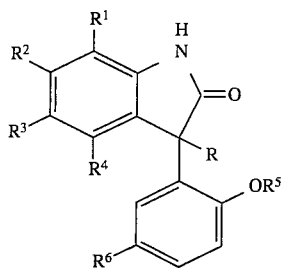

wherein

R is hydrogen, hydroxy or fluoro;

$R^1$, $R^2$, $R^3$ and $R^4$ each are independently hydrogen, C1–4 alkyl, halogen, trifluoromethyl, phenyl, p-methylphenyl or p-trifluoromethylphenyl; or $R^1$ and $R^2$, $R^2$ and $R^3$ or $R^3$ and $R^4$ are joined together to form a benzo fused ring;

$R^5$ is hydrogen or $C_{1-4}$ alkyl; and $R^6$ is chlorine or trifluoromethyl;

or a nontoxic pharmaceutically acceptable salt, solvate or hydrate thereof.

The present invention also provides a method for the treatment or alleviation of disorders associated with BK channels, especially ischemia, convulsions, asthma, urinary incontinence and traumatic brain injury, which comprises administering together with a conventional adjuvant, carrier or diluent a therapeutically effective amount of a compound of formula I or a nontoxic pharmaceutically acceptable salt, solvate or hydrate thereof.

The term "$C_{1-4}$ alkyl" as used herein and in the claims (unless the context indicates otherwise) mean straight or branched chain alkyl groups such as methyl, ethyl, propyl, isopropyl, butyl, isobutyl, t-butyl. Preferably, these groups contain from 1 to 2 carbon atoms. Unless otherwise specified, the term "halogen" as used herein and in the claims is intended to include bromine, chlorine, iodine and fluorine while the term "halide" is intended to include bromide, chloride and iodide anion.

As the compounds of the present invention may possess an asymmetric carbon atom at the 3-position of the oxindole ring, the present invention includes the racemate as well as the individual enantiometric forms of the compounds of Formula I as described herein and in the claims. The use of a single designation such as (3R) or (3S) is intended to include mostly one stereoisomer. Mixtures of isomers can be separated into individual isomers according to methods which are known per se, e.g. fractional crystallization, adsorption chromatography or other suitable separation processes. Resulting racemates can be separated into antipodes in the usual manner after introduction of suitable salt-forming groupings, e.g. by forming a mixture of diastereosiomeric salts with optically active salt-forming agents, separating the mixture into diastereomeric salts and converting the separated salts into the free compounds. The possible enantiomeric forms may also be separated by fractionation through chiral high pressure liquid chromatography columns. Alternatively, the optically active enantiomers of the compounds of Formula I may be prepared by stereoselective synthetic procedures, some of which are described herein. The use of optically active reagents in combination with the appropriate intermediate described herein would produce the desired enantiomer of the compound of Formula I.

The term "nontoxic pharmaceutically acceptable salt" as used herein and in the claims is intended to include nontoxic base addition salts with inorganic bases. Suitable inorganic bases such as alkali and alkaline earth metal bases include metallic cations such as sodium, potassium, magnesium, calcium and the like.

Certain of the compounds of the present invention can exist in unsolvated forms as well as solvated forms including hydrated forms such as monohydrate, dihydrate, hemihydrate, trihydrate, tetrahydrate and the like. The products may be true solvates, while in other cases, the products may merely retain adventitious solvent or be a mixture of solvate plus some adventitious solvent. It should be appreciated by those skilled in the art that solvated forms are equivalent to unsolvated forms and are intended to be encompassed within the scope of the present invention.

In the method of the present invention, the term "therapeutically effective amount" means the total amount of each active component of the method that is sufficient to show a meaningful patient benefit, i.e., healing of acute conditions characterized by openers of large conductance calcium-activated $K^+$ channels or increase in the rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases, tissue damage and/or symptoms associated with dysfunction of cellular membrane polarization and conductance.

The compounds of Formula I may be prepared by various procedures such as those illustrated herein in the examples, in the reaction schemes and variations thereof which would be evident to those skilled in the art. The various oxindole derivatives of Formula I may advantageously be prepared from isatin intermediates which are generally well-known and a general method of preparation is illustrated in Reaction Scheme 1 and a specific example in Reaction Scheme 2.

In the process for the preparation of isatin intermediates of the Formula VII, a number of commonly known and well-established procedures may be employed such as those described by Sandmeyer, T., *Helv. Chim. Acta*, 2, 234 (1919); Stolle, R., *J. Prakt. Chem.*, 105, 137 (1922); and Gassman, P., et al., *J. Org. Chem.*, 42, 1344 (1977). However, a more preferred method for the preparation of isatins of Formula VII starting from the appropriately substituted anilines of Formula V is generally described by Hewawasam, P., et al., *Tetrahedron Lett.*, 35, 7303 (1994) and is illustrated in Reaction Scheme 1. This method appears to be insensitive to the electronic nature of substituents bound to the aromatic ring and is characterized by predictable regiochemical control.

REACTION SCHEME 1

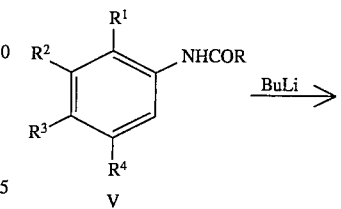

-continued
REACTION SCHEME 1

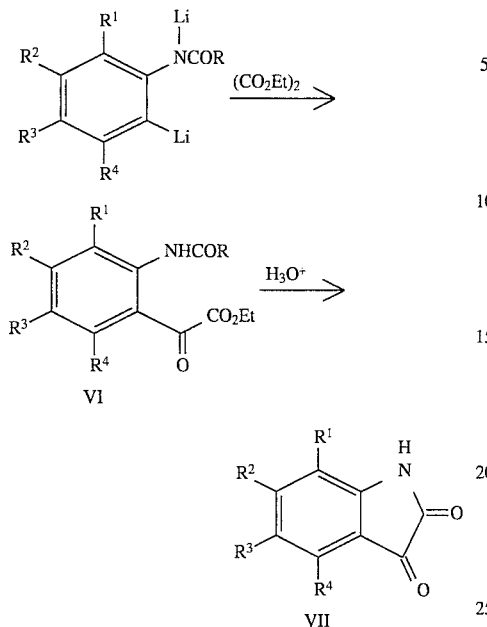

REACTION SCHEME 2

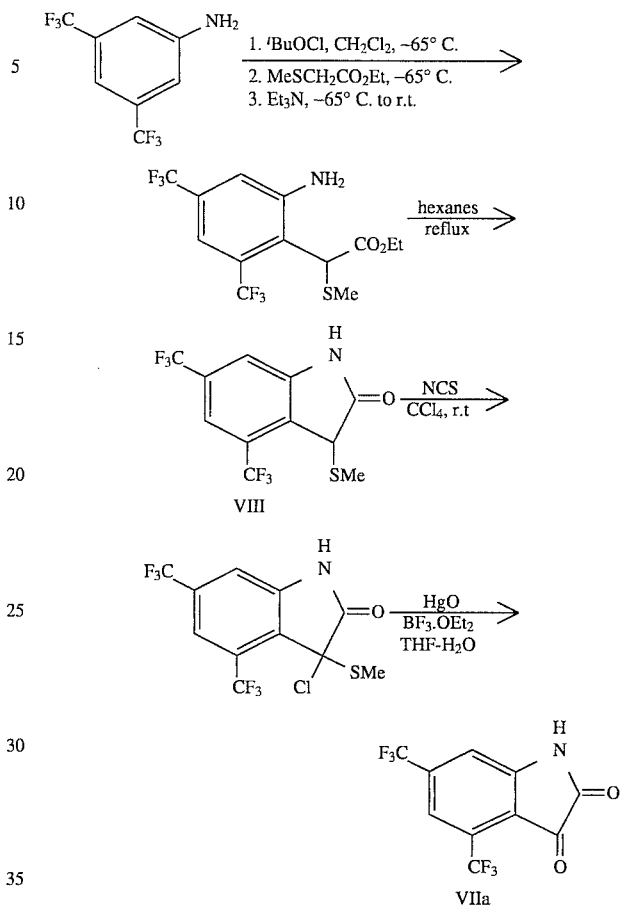

It will be appreciated by those skilled in the art that when the amino group of an aniline compound of Formula V is suitably protected such as with N-pivaloyl and N-(tert-butoxycarbonyl) protecting groups, it can direct metalation to the ortho position. Once the dianions are formed, the reaction with about 1.2 equivalents of diethyl oxalate at low tempeatures such as −78° C. may be used to introduce an α-ketoester moiety ortho to the protected amino group of the aniline derivative to produce the compound of Formula VI. Removal of the protecting group followed by spontaneous cyclization will advantageously produce the isatin of Formula VII. To elaborate further on the process of Reaction Scheme 1, the dianions of N-pivaloylanilines or N-(tert-butoxycarbonyl) anilines are advantageously generated using about 2.2 to 2.4 fold excess of a variety of butyllithium reagants, such as n-butyl-, s-butyl- and t-butyl-lithium reagents in THF at about 0° to −40° C. for 2 to 7 hours.

In a typical procedure, neat dry diethyl oxalate (1.2 equivalents) was added to a solution of the dianion stirred at −78° C. under nitrogen. After being stirred for 30–45 minutes, the reaction was quenched with 1N HCl and diluted with ether to afford the compound of Formula VI. Although the intermediate α-ketoesters of Formula VI may be purified for purposes of characterization, this step is not necessary and the crude product can be advantageously deprotected directed to afford the isatins in excellent overall yield. Deprotection of the N-(tert-butoxycarbonyl) or pivaloyl moieties may be carried out using 3N HCl/THF or 12N HCl/DME, respectively, at reflux temperature. Upon evaporation of the volatile solvents, the isatins generally precipitated from the aqueous residue and isolated by filtration.

An alternative method for the preparation of isatins using the method of Gassman, et al is illustrated in Reaction Scheme 2 for the preparation of 4,6-bis(trifluoromethyl) isatin of the Formula VIIa.

As shown in Reaction Scheme 2, N-chlorination of 3,5-bis(trifluoromethyl)aniline with freshly prepared tert-butyl hypochlorite followed by consecutive addition of ethyl (methylthio)acetate and triethylamine gave the aminoester which, upon heating in boiling hexanes, underwent cyclization to afford the (methylthio)indolone of the Formula VIII. Chlorination of the compound of Formula VIII with N-chlorosuccinimide (NCS) gave the corresponding α-chloro(m-ethylthio)indolone which upon hydrolysis with HgO-BF₃JDO OEt₂ in THF-H₂O gave the desired isatin of Formula VIIa.

Isatins of Formula VII, prepared as described in the above Reaction Schemes 1 and 2 or by well-known literature procedures, were converted to the hydroxyindolones of Formulas IIa and IIb as shown in Reaction Scheme 3. Addition of a THF solution of either a Grignard or aryllithium reagent derived in-situ from an anisole, to the sodium salt of the isatin of Formula VII conveniently prepared with NaH in THF, gave the desired hydroxyindolones of Formula IIa. Most of the hydroxyindolones were purified by either recrystallization or trituration with suitable organic solvents. Demethylation of the methyl ether moiety of the compound of Formula IIa with BBr₃ in CH₂Cl₂ under carefully controlled conditions from −78° to 0° C. afforded the desired phenols of Formula IIb. It was found that the reaction should advantageously not be warmed above 0° C. and, after completion of the demethylation, quenching of the reaction with saturated NaHCO₃ followed by acidification with dilute HCl is required before extracting into an organic solvent to afford the hydroxyindolones of Formula IIb.

REACTION SCHEME 3

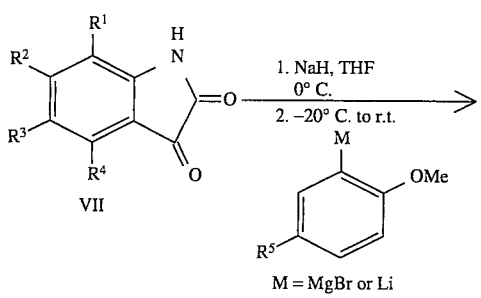

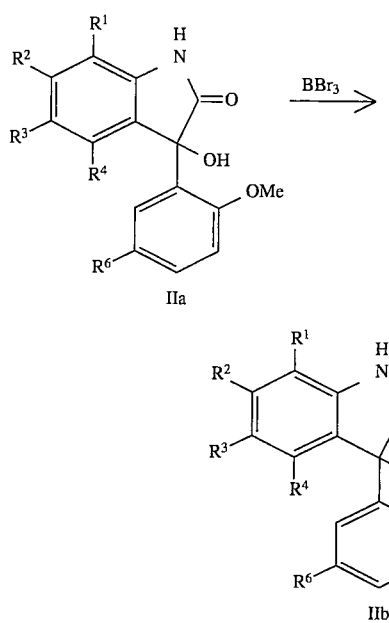

An alternative and more direct approach to the hydroxyindolones of Formula IIb was developed by the addition of magnesium phenolates to isatins of Formula VII as illustrated in Reaction Scheme 4.

REACTION SCHEME 4

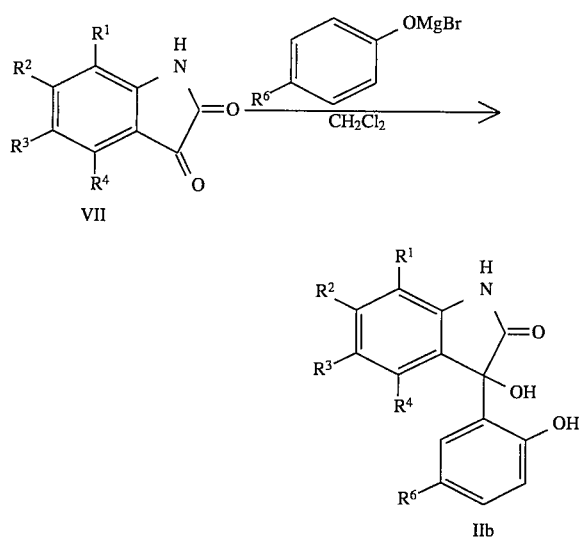

Unlike the process described in Reaction Scheme 3 involving Grignard addition reaction followed by demethylation of the methyl ether product, the free phenol of Formula IIb is directly obtained by this alternate route. The process of Reaction Scheme 4 which involves the reaction of magnesium phenolates prepared by mixing the desired phenol and ethyl magnesium bromide with isatins of Formula VII in methylene chloride, toluene or DMF advantageously afforded the desired hydroxyindolone of Formula IIb. Further, it was found that a variety of electron-deficient magnesium phenolates could be added to the isatins of Formula VII in an advantageously convenient one-pot reaction to directly produce the hydroxyindolones of Formula IIb.

When it is desired to prepare the indolones of Formulas IIIa and IIIb, the corresponding hydroxyindolone of Formula IIa is selectively dehydroxylated with triethylsilane and trifluoroacetic acid (TFA) as illustrated in Reaction Scheme 5.

REACTION SCHEME 5

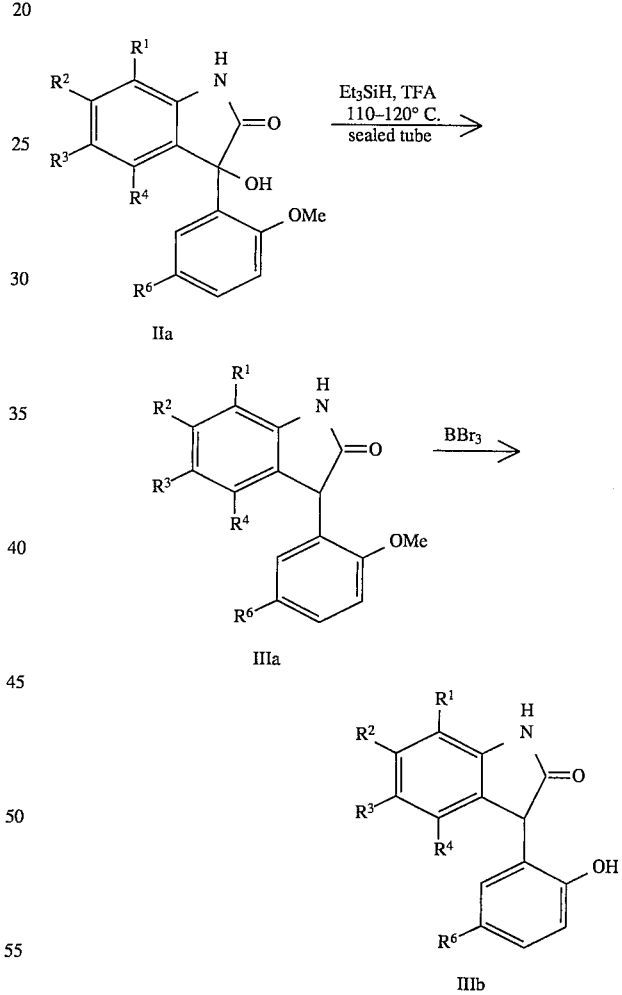

The deoxygenation was carried out in refluxing dichloroethane for several days and additional amounts of TFA were added to replenish any losses. More preferably, the deoxygenation was carried out in a sealed tube with neat triethylsilane and TFA at about 110°–120° C. As will be appreciated by those skilled in the art, the rate of deoxygenation was dependent upon the electronic nature of the substituents present in the hydroxyindolone of Formula IIa and unsubstituted and electron-rich compounds of Formula IIa deoxygenated much more readily compared to electron-deficient compounds of Formula IIa. Demethylation of the methyl ether moiety of the compound of Formula IIIa with BBR$_3$ in CH$_2$Cl$_2$ under carefully controlled conditions from −78° C. to 0° C. afforded the corresponding phenol of Formula IIIb.

In an alternate route to the indolone of Formula IIIa which avoids the use of triethylsilane and trifluoroacetic acid at temperatures of 110°–120° C. for several days is illustrated in Reaction Scheme 6. The process depicted in Reaction Scheme 6 illustrates the preparation of a specific indolone of Formula IIIc, wherein R$^1$, R$^3$ and R$^4$ are hydrogen, R$^2$ is trifluoromethyl and R$^6$ is chloro. Thus, chlorination of commercially available 2-methoxyphenylacetic acid with SO$_2$Cl$_2$ in acetic acid gave 5-chloro-2methoxyphenylacetic acid which was converted to the methyl ester of Formula X using dimethyl sulfate and anhydrous K$_2$CO$_3$ in CH$_3$CN. Reaction of the potassium enolate of ester of Formula X with 4-fluoro-3-nitrobenzotrifluoride in the presence of one equivalent of additional potassium bis(trimethylsilyl)amide (KHMDS) in THF at −78° C. resulted in formation of a dark blue solution of potassium enolate of Formula XI and acidic workup of the reaction provided the desired ester of Formula XI in 75% yield. Upon reduction of the nitro group in the compound of Formula XI with iron in acetic acid, the resultant anilino-ester spontaneously cyclized to provide the desired indolone of Formula IIIc in 84% recrystallized yield.

REACTION SCHEME 6

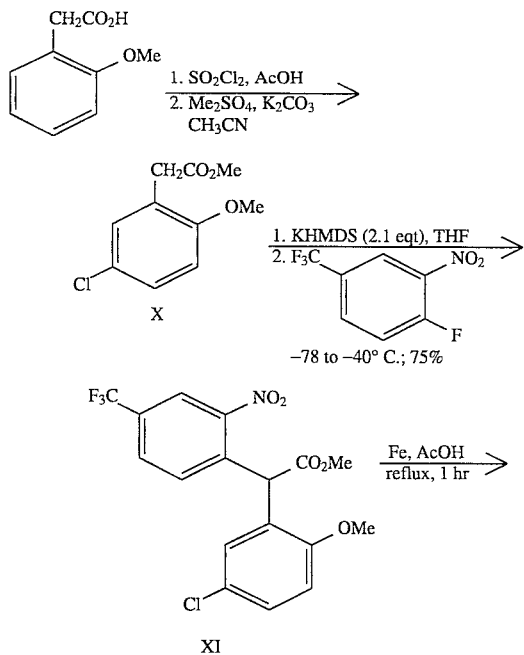

REACTION SCHEME 6 -continued

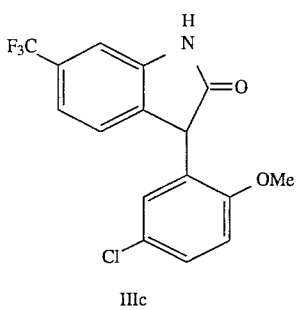

When it is desired to prepare the fluoroindolones of Formula IV, the corresponding hydroxyindolone of Formula IIa is reacted with diethylaminosulfur trifluoride (DAST) as illustrated in Reaction Scheme 7. Preferably, the reaction with DAST is carried out in an organic solvent such as methylene chloride at a temperature of about −78 to 0° C. It should be appreciated by those skilled in the art that the hydroxyindolone of Formula IIa will thereby produce the corresponding fluoroindolone of Formula IV.

The substantially pure enantiomeric forms of the fluoroindolone of Formula IV may readily be obtained by the separation of the racemic mixture using chiral high pressure liquid chromatography methods as described herein and by other well-known methods.

REACTION SCHEME 7

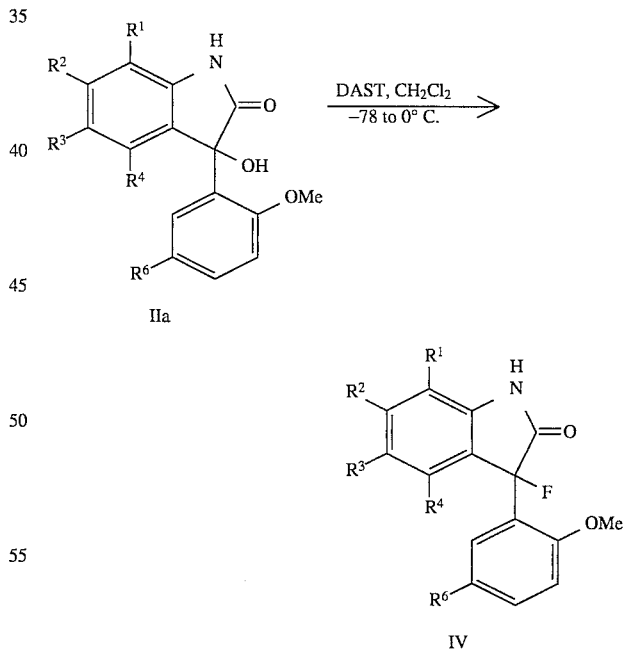

When it is desired to prepare the substantially enantiomeric pure form of the hydroxyindolone of Formulas IIa and IIb, the corresponding indolone of Formula IIIa is selectively oxidized using the appropriate commerically available chiral (+)-(2R, 8aS)- or (−)-(2S, 8aR)-(camphorsulfonyl)oxaziridine of Formula IXa or IXb, respectively as illustrated in Reaction Scheme 8.

REACTION SCHEME 8

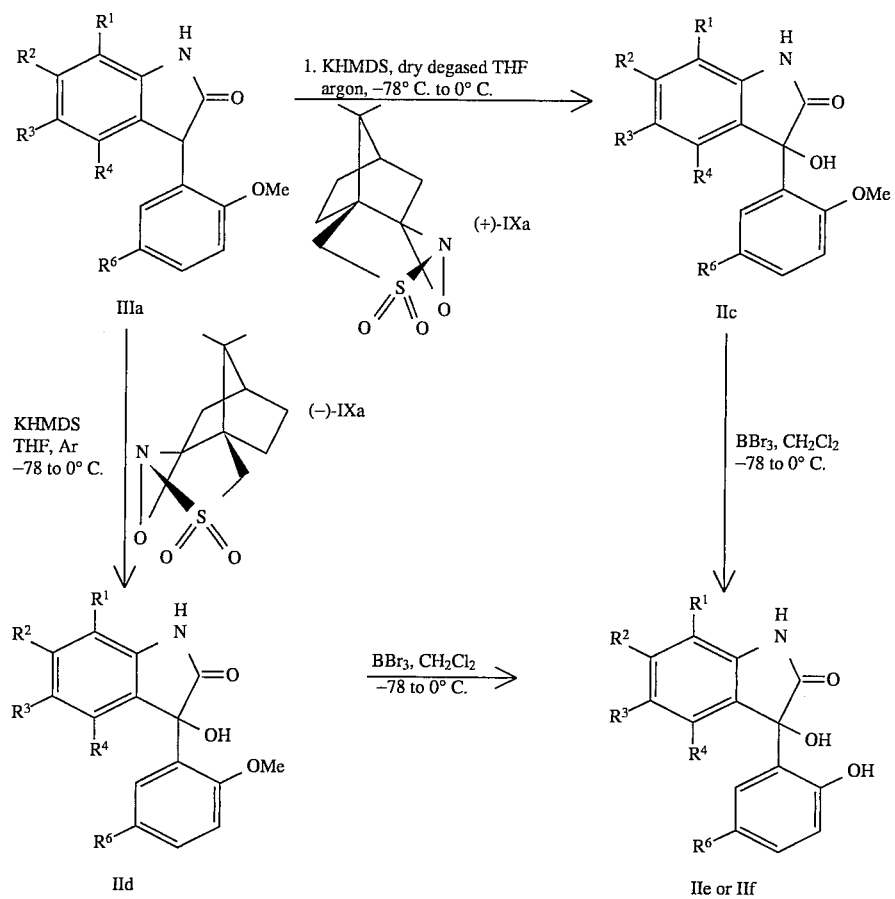

In the process of Reaction Scheme 8, the hydroxylation of the indolone of Formula IIa is treated with potassium bis(trimethylsilyl)amide (KHMDS) in THF and the resulting potassium enolate of the indolone of Formula IIIa is oxidized with the chiral oxaziridine IXa or IXb at about −78° C. followed by gradual warming to 0° C. and then quenching with glacial acetic acid gave the desired corresponding hydroxyindolone of Formula IIc or IId, respectively in high yield and high enantiomeric purity as determined by the application of the NMR chiral-shift solvent (L)-trifluoromethylphenyl carbinol. In the hydroxylation process of Reaction Scheme 8, it is most preferred to utilize degassed dry THF under an argon atmosphere to prevent hydroxylation with molecular oxygen and retain a high degree of asymmetric hydroxylation. Finally, the methyl ether moieties of hydroxyindolones of Formula IIc and IId may be demethylated with BBr₃ in methylene chloride to afford the corresponding phenols of Formula IIe and IIf, respectively. In a specific example described herein, the compound of Example 12 and the compound of Example 13 were each prepared with greater than 95% enantiomeric purity.

In a preferred embodiment of the invention the compounds of Formula II have the formula

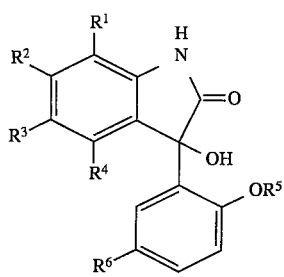

wherein $R^1$, $R^2$, $R^3$ and $R^4$ each are independently hydrogen, methyl, halogen, or trifluoromethyl, and when $R^1$, $R^3$ and $R^4$ are hydrogen, $R^2$ is phenyl, p-methylphenyl or trifluoromethylphenyl; or $R^1$ and $R^2$, $R^2$ and $R^3$ or $R^3$ and $R^4$ are joined together to form a benzo fused ring; $R^5$ is hydrogen or methyl; and $R^6$ is chlorine or trifluoromethyl; or a nontoxic pharmaceutically acceptable salt, solvate or hydrate thereof.

In another preferred embodiment of the invention the compounds of Formula III have the formula

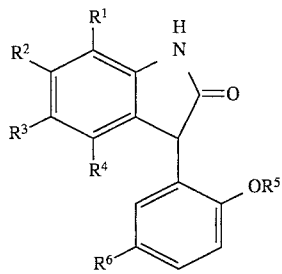

wherein $R^1$, $R^2$, $R^3$ and $R^4$ each are independently hydrogen, methyl, halogen, or trifluoromethyl, and when $R^1$, $R^3$ and $R^4$ are hydrogen, $R^2$ is phenyl, p-methylphenyl or trifluoromethylphenyl; or $R^1$ and $R^2$, $R^2$ and $R^3$ or $R^3$ and $R^4$ are joined together to form a benzo fused ring; $R^5$ is hydrogen or methly; and $R^6$ is chlorine or trifluoromethyl; or a nontoxic pharmaceutically acceptable salt, solvate or hydrate thereof.

In still another preferred embodiment of the invention the compounds of Formula IV have the formula

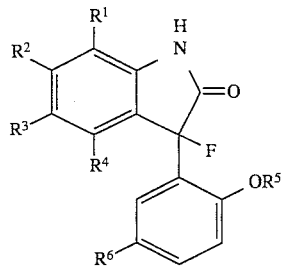

wherein $R^1$, $R^2$, $R^3$ and $R^4$ each are independently hydrogen, methyl, halogen, or trifluoromethyl, and when $R^1$, $R^3$ and $R^4$ are hydrogen, $R^2$ is phenyl, p-methylphenyl or trifluoromethyl; or $R^1$ and $R^2$, $R^2$ and $R^3$ or $R^3$ and $R^4$ are joined together to form a benzo fused ring; $R^5$ is $C_{1-4}$ alkyl; and $R^6$ is chlorine or trifluoromethyl; or a nontoxic pharmaceutically acceptable salt, solvate or hydrate thereof.

In another aspect, this invention provides a method for the treatment of or protection from disorders which are mediated by opening of the large conductance calcium-activated $K^+$ channels (BK channels)in a mammal in need thereof, which comprises administering to said mammal a therapeutically effective amount of a compound of Formula I or a nontoxic pharmaceutically acceptable salt, solvate or hydrate thereof. Preferably, the compounds of Formula I are useful in the treatment of ischemia, convulsions, asthma, urinary incontinence and traumatic brain injury and other disorders sensitive to BK channel activating activity. Most preferably, the compounds of Formula I are useful in the treatment of cerebral ischemia.

In still another aspect, this invention provides pharmaceutical compositions comprising at least one compound of Formula I in combination with a pharmaceutical adjuvant, carrier or diluent.

BIOLOGICAL ACTIVITY

Potassium ($K^+$) channels are structurally and functionally diverse families of $K^+$-selective channel proteins which are ubiquitous in cells, indicating their central importance in regulating a number of key cell functions [Rudy, B., *Neuroscience*, 25:729–749 (1988)]. While widely distributed as a class, $K^+$ channels are differentially distributed as individual members of this class or as families. [Gehlert, D. R., et al., *Neuroscience*, 52: 191–205 (1993)]. In general, activation of $K^+$ channels in cells, and particularly in excitable cells such as neurons and muscle cells, leads to hyperpolarization of the cell membrane, or in the case of depolarized cells, to repolarization. In addition to acting as an endogenous membrane voltage clamp, $K^+$ channels can respond to important cellular events such as changes in the intracellular concentration of ATP or the intracellular concentration of calcium ($Ca^{2+}$). The central role of $K^+$ channels in regulating numerous cell functions makes them particularly important targets for therapeutic development. [Cook, N. S., Potassium channels: Structure, classification, function and therapeutic potential. Ellis Horwood, Chinchester (1990)]. One class of K+ channels, the large-conductance $Ca^{2+}$-activated $K^+$ channels (maxi-K or BK channels), is regulated by transmembrane voltage, intracellular $Ca^{2+}$, and a variety of other factors such as the phosphorylation state of the channel protein. [Latorre, R., et al., *Ann. Rev. Pysiol.*, 51:385–399 (1989)]. The large, single channel-conductance (generally>150 pS) and high degree of specificity for $K^+$ of BK channels indicates that small numbers of channels could profoundly affect membrane conductance and cell excitability. Additionally, the increase in open probability with increasing intracellular $Ca^{2+}$ indicates involvement of BK channels in the modulation of $Ca^{2+}$-dependent phenomena such as secretion and muscular contraction. [Asano, M., et al., *J. Pharmacol. Exp. Ther.*, 267:1277–1285 (1993)].

Openers of BK exert their cellular effects by increasing the open probability of these channels [McKay, M. C., et al., *J. Neurophysiol.*, 71: 1873–1882 (1994); and Olesen, S.-P., *Exp. Opin. Invest. Drugs*, 3:1181–1188 (1994)]. This increase in the opening of individual BK channels collectively results in the hyperpolarization of cell membranes, particularly in depolarized cells, produced by significant increases in whole-cell BK-mediated conductance.

The ability of compounds described in the present invention to open BK channels and increase whole-cell outward ($K^+$) BK-mediated currents was assessed under voltage-clamp conditions by determining their ability to increase cloned mammalian (mSlo or hSlo) BK- mediated outward current heterologously expressed in Xenopus oocytes [Butler, A., et al., *Science*, 261:221–224 (1993); and Dworetzky, S. I., et al., *Mol. Brain Res.*, 27:189–193 (1994)]. The two BK constructs employed represent nearly structurally identical homologous proteins, and have proven to be pharmacologically identical in our tests. To isolate BK current from native (background, non-BK) current, the specific and potent BK channel-blocking toxin iberiotoxin (IBTX) [Galvez, A., et al., *J. Biol. Chem*, 265:11083–11090 (1990)] was employed at a supramaximal concentration (50 nM). The relative contribution of BK channels current to total outward current was determined by subtraction of the current remaining in the presence of IBTX (non-BK current) from the current profiles obtained in all other experimental conditions (control, drug, and wash). It was determined that at the tested concentration the compounds profiled did not effect non-BK native currents in the oocytes. All compounds were tested in at least 5 oocytes and are reported at the single concentration of 20 uM; the effect of the selected compounds of Formula I on BK current was expressed as the percent of control IBTX-sensitive current and is listed in Table I. Recordings were accomplished using standard two-electrode voltage clamp techniques [Stuhmer, W., et al., *Methods in Enzymology*, Vol. 207:319–339 (1992)]; voltage-clamp protocols consisted of 500–750 ms duration step depolarizations from a holding potential of –60 mV to +140 mV in 20 mV steps. The experimental media (modified Barth's solution) consisted of (in mM): NaCl(88), NaHCO3(2.4), KCl(1.0), HEPES (10), MgSO4(0.82), Ca(NO3)2 (0.33), CaCl2(0.41); pH 7.5.

TABLE I

Effect of Selected Compounds on BK Channels

| Example No. | BK Current* |
| --- | --- |
| 1 | + |
| 3 | ++ |
| 4 | +++ |
| 6 | + |
| 7 | + |
| 9 | ++ |
| 13 | ++ |
| 14 | ++ |
| 15 | +++ |
| 16 | +++ |
| 22 | +++ |
| 25 | + |
| 31 | + |
| 33 | +++ |

*at 20 µM expressed as percent of controls;
+ = 100–125%
++ = 125–150%
+++ = >150%

The compound of Example 3 was also examined with single-channel inside-out excised patches from both COS cells stably transfected with mSlo and with patches from oocytes expressing hSlo and was found to effectively increase the open probability in both systems at a concentration of 1 µM. Other compounds were examined using whole-cell and single-channel patch-clamp techniques in HEK 293 cells transiently and stably expressing hSlo BK channels at high levels, for example, the compounds of Examples 14, 37 and 38 were found to be very potent and effective openers of hSlo BK channels under whole-cell and (inside out and outside-out) excised patch clamp recording conditions.

To determine the ability of these compounds to reduce cell loss resulting from neuronal ischemia, a standard rodent model of permanent focal ischemia, involving occlusion of the middle cerebral artery in the spontaneously hypertensive rat (MCAO model) was employed [Tamura, A., et al., *Journal of Cerebral Blood Flow and Metabolism.*, Volume 1, 53–60, (1981)].

Selected compounds have been evaluated in the focal stroke model involving permanent middle cerebral artery occlusion (MCAO) in the spontaneously hypertensive rat. This procedure results in a reliably large neocortical infarct volume that is measured by means of vital dye exclusion in serial slices through the brain 24 hours after MCAO. In the present test, compounds were administered using an i.v. or i.p. route of administration at two hours after occlusion. For example, in this model, the compound of Example 4 reduced the cortical infarct volume by about 18% when administered intravenously (0.03 mg/kg) and about 26% when administered intraparitoneally (10 mg/kg) as a single bolus 2 hours after middle cerebral artery occlusion as compared to vehicle-treated (2% DMSO, 98% PG) control. Also, in this model, the compound of Example 14 reduced the cortical infarct volume by about 18% when administered intravenously (0.3 mg/kg) as a single bolus 2 hours after middle cerebral artery occlusion as compared to vehicle-treated (2% DMSO, 98% PG) control.

The results of the above in vitro and in vivo tests demonstrate that the compounds of the instant invention are potent openers of the large-conductance calcium-activated $K^+$ channels (maxi-K or BK channels). Thus, the compounds of the present invention are useful for the treatment of human disorders arising from dysfunction of cellular membrane polarization and conductance and, preferably, are indicated for the treatment of ischemia, convulsions, asthma, urinary incontinence and traumatic brain injury and other disorders sensitive to BK channel activating activity. Most preferably, the compounds of Formula I are useful in the treatment of cerebral ischemia.

Therefore, the compounds of Formula I or pharmaceutical compositions thereof are useful in the treatment, alleviation or elimination of disorders or other disorders associated with the BK channels. Such disorders include ischemia, convulsions, asthma, urinary incontinence and traumatic brain injury, and other disorders sensitive to potassium channel openers.

In another embodiment, this invention includes pharmaceutical compositions comprising at least one compound of Formula I in combination with a pharmaceutical adjuvant, carrier or diluent.

In still another embodiment, this invention relates to a method of treatment or prevention of disorders responsive to opening of potassium channels in a mammal in need thereof, which comprises administering to said mammal a therapeutically effective amount of a compound of Formula I or a nontoxic pharmaceutically acceptable salt, solvate or hydrate thereof.

In yet another embodiment, this invention relates to a method for treating an ischemic condition in a mammal in need thereof, which comprises administering to said mammal a therapeutically effective amount of a compound of Formula I or a non-toxic pharmaceutically acceptable salt, solvate or hydrate thereof.

For therapeutic use, the pharmacologically active compounds of Formula I will normally be administered as a pharmaceutical composition comprising as the (or an) essential active ingredient at least one such compound in association with a solid or liquid pharmaceutically acceptable carrier and, optionally, with pharmaceutically acceptable adjuvants and excipients employing standard and conventional techniques.

The pharmaceutical compositions include suitable dosage forms for oral, parenteral (including subcutaneous, intramuscular, intradermal and intravenous) bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. Particularly useful is the administration of a compound of Formula I directly in parenteral formulations. The pharmaceutical compositions are prepared by conventional techniques appropriate to the desired preparation containing appropriate amounts of the active ingredient, that is, the compound of Formula I according to the invention. See, for example, *Remington's Pharmaceutical Sciences*, Mack Publishing Company, Easton, Pa., 17th edition, 1985.

The dosage of the compounds of Formula I to achieve a therapeutic effect will depend not only on such factors as the age, weight and sex of the patient and mode of administration, but also on the degree of potassium channel activating activity desired and the potency of the particular compound being utilized for the particular disorder of disease concerned. It is also contemplated that the treatment and dosage of the particular compound may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

A suitable dose of a compound of Formula I or pharmaceutical composition thereof for a mammal, including man, suffering from, or likely to suffer from any condition as described herein is an amount of active ingredient from about 0.1 µg/kg to 100 mg/kg body weight. For parenteral administration, the dose may be in the range of 1 µg/kg to 10 mg/kg body weight for intravenous administration The active ingredient will preferably be administered in equal doses from one to four times a day. However, usually a small dosage is administered, and the dosage is gradually increased until the optimal dosage for the host under treatment is determined.

However, it will be understood that the amount of the compound actually administered will be determined by a physician, in the light of the relevant circumstances including the condition to be treated, the choice of compound of be administered, the chosen route of administration, the age, weight, and response of the individual patient, and the severity of the patient's symptoms.

The following examples are given by way of illustration and are not to be construed as limiting the invention in any way inasmuch as many variations of the invention are possible within the spirit of the invention.

DESCRIPTION OF SPECIFIC EMBODIMENTS

In the following examples, all temperatures are given in degrees Centigrade. Melting points were recorded on a Gallenkamp capillary melting point apparatus and boiling points were measured at specific pressures (mm Hg) and both temperatures are uncorrected. Proton magnetic resonance ($^1$H NMR) and carbon magnetic resonance ($^{13}$C NMR) spectra were recorded on a Bruker AC 300 and fluorine magnetic resonance (19F NMR) were recorded on a Bruker AM 300, equipped with a QNP probe. All spectra were determined in the solvents indicated and chemical shifts are reported in δ units downfield from the internal standard tetramethylsilane (TMS) and interproton coupling constants are reported in Hertz (Hz). Splitting patterns are designated as follows: s, singlet; d, doublet; t, triplet; q, quartet; m, multiplet; br, broad peak; dd, doublet of doublet; bd, broad doublet; dr, doublet of triplet; bs, broad singlet; dq, doublet of quartet. Infrared (IR) spectra using potassium bromide (KBr) were determined on a Perkin Elmer 781 spectrometer from 4000 cm$^{-1}$ to 400 cm$^{-1}$, calibrated to 1601 cm$^{-1}$ absorption of a polystyrene film and reported in reciprocal centimeters (cm$^{-1}$). Optical rotations $[\alpha]_D^{25}$ were determined on a Perkin-Elmer 41 polarimeter in the solvents indicated. Low resolution mass spectra (MS) and the apparent molecular (MH$^+$) or (M–H)$^-$ was determined on a Finnigen TSQ 7000. The element analysis are reported as percent by weight.

The following preparations Nos. 1–5 illustrate representative actual procedures for the preparation of intermediates and methods for the preparation of products according to this invention. It should also be evident to those skilled in the art that appropriate substitution of both the materials and methods disclosed herein will produce the examples illustrated below and those encompassed by the scope of this invention.

Preparation No. 1

6-(Trifluoromethyl)-1H-indol-2,3-dione

A stirred neat mixture of 3-aminobenzotrifluoride (82.4 g, 0.51 mol) and (Boc)$_2$O (123 g, 0.56 mol) was heated at 80° C. for 2–3 hours until CO$_2$ evolution was ceased. The mixture was allowed to cool and the tBuOH was rotary evaporated. The resultant white solid was recrystallized from hexanes to provide white needles (119 g, 89%) of N-(tert-butoxycarbonyl)aminobenzotrifluoride.

Sec-BuLi (338 mL, 0.44 mol, 1.3M in cyclohexane) was added over 20 minutes to a cold (−78° C.) stirred solution of N-Boc-aminobenzotrifluoride (52.25 g, 0.2 mol) in dry THF (200 mL) under nitrogen. The resultant yellow partial solution was warmed to −45°—−40° C. and maintained for 2 hrs. The resultant thick yellow slurry of the dianion was cooled to −78° C. and neat dry diethyl oxalate (35.1 g, 0.24 mol) was added rapidly. The resultant orange-brown solution was stirred at −78° C. for 1 hour. The reaction was diluted with ether (200 mL) and quenched with 3N HCl (150 mL) and then allowed to warm to room temperature. The organic layer was separated, washed with water, brine and then dried (Na$_2$SO$_4$). Evaporation of solvents gave a golden-yellow oil (80.7 g) which was flash chromatographed (silica gel/ CH$_2$Cl$_2$) to afford the pure keto-ester (61.1 g, 85%): IR (film, cm$^{-1}$) 3320, 1740, 1670, 1540, 1370, 1340, 1250, 1140; $^1$H NMR (300 MHz, CDCl$_3$)δ 1.40 (3 H, t, J=7.1 Hz), 1.51 (9 H, s), 4.45 (2 H, q, J=7.1 Hz), 7.25 (1 H, d, J=8.3 Hz) 7.79 (1 H, d, J=8.3 Hz), 8.86 (1 H, s), 10.40 (1 H, brd s); MS m/e 362 (MH$^+$).

A stirred solution of the keto-ester (57 g, 0.158 mol) in THF (1 L) and 3N HCl (250 mL) was heated to reflux for 6 hours. The mixture was allowed to cool and the THF was rotary evaporated. The resultant orange suspension was allowed to cool. The solid was filtered, washed with water and then air dried overnight to afford the desired 6-(trifluoromethyl)isatin (29.6 g, 87%): mp 196°–198° C.; IR (KBr, cm$^{-1}$) 3100, 1750, 1710, 1320, 1170, 1125; $^1$H NMR(300 MHz, DMSO-d$_6$)δ 7.09 (1 H,s),7.39(1H,d,J=7.7 Hz), 7.68 (1 H, d, J=7.7 Hz), 11.26 (1 H, brd s); MS m/e 216 (MH$^+$).

Anal. calcd. for C$_9$H$_4$F$_3$NO$_2$: C,50.28 H, 1.91; N, 6.47.

Found: C, 50.25; H, 1.87; N, 6.51.

The following isatin was prepared according to a similar procedure.

5-(Trifluoromethyl)-1H-indol-2,3-dione: mp 188°–190° C.

Preparation No. 2

4,6-bis-(Trifluoromethyl)-1H-indol-2,3-dione

Freshly prepared 'BuOCl (2.2 g, 20 mmol) was added dropwise to a stirred cold (−65° C.) solution of 3,5-bis-(trifluoromethyl)aniline (4.58 g, 20 mmol) in anhydrous $CH_2Cl_2$ (25 mL). After 10 minutes, neat ethyl (methylthio) acetate (2.68 g, 20 mmol) was added and the mixture stirred at −65° C. for 1 hr. Triethylamine (2.68 g, 20 mmol) was added and then the mixture was allowed to warm to room temperature. The reaction mixture was quenched with water, the organic layer was separated and then rotary evaporated. The oily residue (6.35 g) was dissolved in hexanes and boiled for several hours and then allowed to cool. The precipitated beige solid was filtered and washed with hexanes to afford 3.67 g of pure (methylthio) indolone intermediate.

N-chlorosuccinimide (1.31 g, 9.8 mmol) was added to a stirred solution of (methylthio) indolone (2.95 g, 9.4 mmol) in $CCl_4$ (150 mL). The mixture was stirred at room temperature for 6.5 hours. The suspension was filtered, washed with $CCl_4$ and the filtrate was rotary evaporated at 25°–30° C. The residual light-brown oil was dissolved in a minimum volume (~5–10 mL) of $CCl_4$ and kept in an ice bath. The precipitated last traces of succinimide were filtered and washed with hexanes. Evaporation of the filtrate gave a red-brown oil (3.56 g) of α-chlorooxindole which was used in the next step without further purification.

Neat $BF_3 \cdot OEt_2$ (1.16 mL, 9.4 mmol) was added to a stirred suspension of HgO in 4:1 THF-H2O (100 mL). A solution of the α-chlorooxindole (3.56 g) in THF (20 mL) was added and the mixture was stirred for 2–3 days. The suspension was filtered through a celite pad and the filtrate was washed with saturated brine and then dried ($Na_2SO_4$). Evaporation of THF gave 3.2 g of crude isatin which was recrystallized from ether to afford pure 4,6-bis-(trifluoromethyl)-1H-indol-2,3-dione (1.27 g): mp 200°–203° C.; IR (KBr, cm$^{-1}$) 1778, 1748, 1278, 1138; $^1$H NMR (300 MHz, DMSO-d$_6$) δ 7.40 (1 H, s), 7.61 (1 H, s), 11.52 (1 H, s); MS m/e 284 (MH$_+$).

The following isatins were prepared according to known literature procedures, P. M. Maginnity, et al., *J. Am. Chem. Soc.*, 73, 3579 (1951) and C. S. Marvel, et al., *Organic Synthesis Coil.* Vol. 1, 327–330.

4-(Trifluoromethyl)-1H-indol-2,3-dione: mp 210°–212° C.

7-(Trifluoromethyl)-1H-indol-2,3-dione: mp 190°–192° C.

4,6-Dichloro-1H-indol-2,3-dione: mp 258°–260° C.

The following isatins can also be prepared by the methods in the cited reference.

1H-Benz[g]indol-2,3-dione: mp 256°–259° C. (dec.) [H. Cassebaum, *Chem. Ber.*, 90, 2876 (1957)].

1H-Benz[f]indol-2,3-dione: mp 250°–255° C. (dec.) [A. Etienne et al., *Bull. Soc. Chem. Fr.*, 6, 743–748 (1954)].

1H-Benz[e]indol-2,3-dione: mp 252°–254° C. (dec.) [W. Wendelin, et al., *J. Het. Chem.*, 24, 1381 (1987)].

6-Phenyl-1H-indol-2,3-dione: mp 230°–235° C. [P. W. Sadler, *J. Org. Chem.*, 21, 169 (1956)].

6-Iodo-1H-indol-2,3-dione: mp 196°–198° C. [Von. W. Langenbeck, et al., *J. Prakt. Chemie.*, 4, IV, 136–146 (1956)].

Preparation No. 3

General Procedure for preparation of 1,3-dihydro-3-hydroxy-3-(2-hydroxyaryl)-2H-indol-2-ones

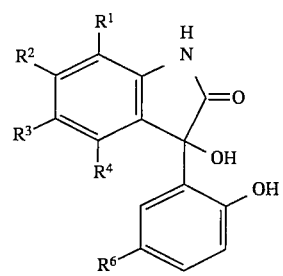

Method A

A solution of the 2-methoxyaryl Grignard reagent (1–2 eqt.) in THF was added to a stirred cold (−20° C.) solution of sodium salt of the isatin in THF under nitrogen. The mixture was allowed to warm to room temperature and maintained until (1–2 hours) the isatin was consumed. The reaction mixture was diluted with ether, cooled in a ice-bath and then quenched with 1N HCl. The organic layer was separated, washed with 0.5N NaOH, water, brine and then dried ($Na_2SO_4$). The crude solid isolated after evaporation of the solvents was triturated with $CH_2Cl_2$ to afford pure 1,3-dihydro-3-hydroxy-3-(2-methoxyaryl)-2H-indol-2-ones in 70–95% yield.

Demethylation of methyl ether moiety of the above product was carried out with $BBR_3$ in $CH_2Cl_2$. To a cold (−78° C.) stirred solution of 1,3-dihydro-3-hydroxy-3-(2-methoxyaryl)-2H-indol-2-one in anhydrous $CH_2Cl_2$, $BBR_3$ (3 eqt.; 1M solution in $CH_2Cl_2$) was added under nitrogen. The mixture was warmed in an ice bath and maintained until starting material disappeared by TLC (1–2 hours). The reaction was quenched with saturated $NaHCO_3$ and then acidified with 1N HCl. When the product is soluble in $CH_2Cl_2$, the organic layer was separated, washed with brine and then dried ($MgSO_4$). If product is insoluble in $CH_2Cl_2$, the organic layer was rotary evaporated at room temperature and the aqueous residue was extracted with EtOAc. The EtOAc extract was washed with brine and then dried ($Na_2SO_4$). Evaporation of the organic solvent gave 1,3-dihydro-3-hydroxy-3-(2-hydroxyaryl)-2H-indol-2-ones.

The crude product was purified by either trituration or recrystallization from a suitable solvent to afford pure product in 80–95% yield.

Method B

Bromomagnesium phenolate was prepared by reacting 1 equivalent of the phenol in ether with one equivalent of ethereal solution of ethyl magnesium bromide at 0° C. and then allowing to warm to room temperature. The resultant suspension of the bromomagnesium phenolate in ether was rotary evaporated at 25° C. to dryness and then dissolved in anhydrous $CH_2Cl_2$. A solution of the isatin (1 eqt) in $CH_2Cl_2$ was added to the bromomagnesium phenolate solution and the mixture stirred at room temperature until the isatin was fully consumed (1–24 hours). The reaction was quenched with either saturated $NH_4Cl$ solution or 1N HCl and then extracted with $CH_2Cl_2$. The crude product was purified by either trituration or recrystallization from a suitable solvent to afford pure 1,3-dihydro-3-hydroxy-3-(2-hydroxyaryl)-2H-indol-2-ones.

Preparation No. 4

General Procedure for preparation of 1,3-dihydro-3-(2-hydroxyaryl)-2H-indol-2-ones

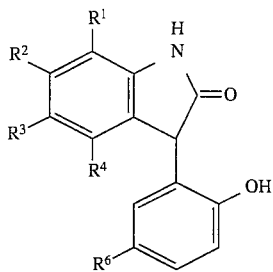

A neat stirred mixture of 1,3-dihydro-3-hydroxy-3-(2-methoxyaryl)-2H-indol-2-one (1 eqt.), triethylsilane (3 eqt.) and trifluoroacetic acid (3 eqt.) was heated at 110°–120° C. in a sealed tube for 1–3 days until deoxygenation was complete by TLC analysis. Excess Et$_3$SiH and TFA were rotary evaporated and the residue was flash chromatographed (silica gel/3% MeOH in CH$_2$Cl$_2$) to afford the desired deoxygenated product 1,3-dihydro-3-(2-methoxyaryl)-2H-indol-2-one (80–90%). Demethylation of the methyl ether moiety was carried out with BBR$_3$ (3 eqt.) at –78° C. to 0° C. followed by usual work up as described in Preparation No. 3 to afford the title product.

Preparation No 5

General Procedure for preparation of 1,3-dihydro-3-fluoro-3-(2-methoxyaryl)-2H-indol-2-ones

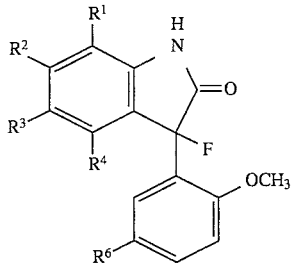

Neat diethylaminosulfur trifluoride (DAST) was added dropwise to a cold (–78° C.) stirred solution or suspension of the 3-aryl-1,3-dihydro-3-hydroxy2H-indol-2-one under nitrogen. The resultant mixture was allowed to warm to 0° C. The progress of the reaction was followed by TLC. The reaction mixture was quenched with water at 0° C. When the product was soluble in CH$_2$Cl$_2$, the organic layer was separated, washed with brine and then dried (MgSO$_4$). If the product is insoluble or partially soluble in CH$_2$Cl$_2$, the organic layer was rotary evaporated at room temperature and the aqueous residue was extracted with EtOAc. The EtOAc extract was washed with brine and then dried (Na$_2$SO$_4$). Evaporation of the organic solvent afforded the 3-aryl-1,3-dihydro-3-fluoro-2H-indol-2-ones. The crude products were purified by either trituration or recrystallization from suitable solvents to afford the pure products in 90–95% yield.

Preparation No. 6

Methyl (5-chloro-2-methoxyphenyl)acetate

Neat SO$_2$Cl$_2$ (30.5 g, 18 mL, 0.225 mol) was added dropwise over 30 minutes to a cold (5° C.) partial solution of (2-methoxyphenyl)acetic acid (25 g, 0.15 mol) in glacial AcOH (500 mL). The mixture was stirred at room temperature for 16 hours and then poured into cold water (2.5 L) with vigorous stirring. The resultant white precipitate was allowed to stand at room temperature for 2–3 hours, then filtered, washed with water and then air dried overnight to afford (5-chloro-2-methoxyphenyl)acetic acid (19.8 g, 66%).

A stirred suspension of (5-chloro-2-methoxyphenyl)acetic acid (10 g, 0.05 mol), anhydrous K$_2$CO$_3$ (8.3 g, 0.06 mol) and dimethyl sulfate (7.6 g, 0.06 mol) in anhydrous CH$_3$CN (60 mL) was heated to reflux under nitrogen for 2 hours. The reaction mixture was allowed to cool and the excess dimethyl sulfate was quenched with Et$_3$N (1 mL) and then filtered. The filtrate was rotary evaporated and the residue was suspended in water and extracted with ether, washed with satd. NaHCO$_3$, water, brine and then dried (Na$_2$SO$_4$). Filtration and evaporation of the ether gave a colorless oil which was distilled in vacuo to afford methyl (5-chloro-2-methoxyphenyl)acetate (10.1 g, 94%): bp 96°–98° C./0.5 torr; IR (film, cm$^{-1}$) 1742, 1250, 1150, 1028; $^1$H NMR (300 MHz, CDCl$_3$)δ 3.56 (2 H, s), 3.66 (3 H, s), 3.76 (3 H, s), 8.75 (16 H, d, J=8.6 Hz), 7.13 (1 H, d, J=2.5 Hz), 7.17 (1 H, dd, J=8.6 and 2.5 Hz); MS m/e 215 (MH$^+$).

EXAMPLE 1

(±)-3-(5-Chloro-2-methoxyphenyl)-1,3-dihydro-3-hydroxy-6(trifluoromethyl)-2H-indol-2-one mp 207°–210° C.; IR (KBr, cm$^{-1}$) 3400, 1730, 1320, 1250, 1125, 1170; $^1$H NMR (300 MHz, DMSO-d$_6$)δ 3.41 (3 H, s), 6.91 (1 H, d, J=0.73 Hz), 6.94 (1 H, s), 7.05 (2 H, m), 7.19 (1 H, d, J=8.2 Hz), 7.35 (1 H, dd, J=8.6 and 2.7 Hz), 7.80 (1 H, d, J=2.7 Hz), 10.67 (1 H, s); $^{13}$C NMR (75 MHz, DMSO-d$_6$)δ 55.95, 74.25, 105.21. 113.52, 118.45, 122.28, 124.27, 124.46, 126.83, 128.70, 129.47 (q), 131.31, 136.60, 143.88, 154.30, 177.29; MS m/e 358 (MH$^+$).

Anal. calcd. for C$_{16}$H$_{11}$ClF$_3$NO$_3$: C, 53.72; H, 3.09; N, 3.83.

Found: C, 53.43; H, 2.99; N, 3.83.

EXAMPLE 2

(±)-3-(5-Chloro-2-methoxyphenyl)-1,3-dihydro-6-(trifluoromethyl)-2H-indol-2-one A stirred suspension of methyl (5-chloro-2-methoxyphenyl)[2-nitro-4-(trifluoromethyl)phenyl]acetate (2.02 g, 5 mmol) and iron powder (1.18 g, 20 mmol) in gla. AcOH (25 mL) was heated to reflux for 1 hour. The suspension was allowed to cool and then poured into cold water (100 mL) with vigorous stirring. The product was extracted with ether (2×50 mL), washed with 6N HCl (50 mL), water, brine and then dried (Na$_2$SO$_4$). Evaporation of ether gave a beige solid (1.8 g) which was triturated with ether to afford the desired product as an off-white solid (1.61 g, 95%): mp 210°–213° C.; IR (KBr, cm$^{-1}$) 3200, 1710, 1320, 1250, 1170, 1120, 1050; $^1$H NMR (300 MHz, DMSO-d$_6$)δ 3.57 (3 H, s), 4.91 (1 H, s) 7.02 (1 H, d, J=8.8 Hz), 7.06 (2 H, m), 7.21, (1 H, dd, J=7.7 and 0.6 Hz), 7.35 (2 H, m), 10.77 (1 H, s); $^{13}$C NMR (75 MHz, DMSO-d$_6$)δ 48.25, 56.07, 105.05. 113.58, 118.26, 122.42, 124.18, 126.03, 127.38, 128.60 (q), 128.70, 130.65, 134.37, 143.58, 156.09, 176.73; MS m/e 342 (MH$^+$).

Anal. calcd. for C$_{16}$H$_{11}$ClF$_3$NO$_2$: C, 56.24; H, 3.24; N, 4.09.

Found: C, 56.37; H, 3.25; N, 4.07.

EXAMPLE 3

(±)-3-(5-Chloro-2-hydroxyphenyl)-1,3-dihydro-3-hydroxy-6-(trifluoromethyl)-2H-indol-2-one mp 210°–213° C.; IR (KBr, cm$^{-1}$) 3300, 1725, 1320, 1250, 1170, 1140; $^1$H NMR (300 MHz, DMSO-d$_6$)δ 6.61 (1 H, dd, J=8.5 and 2.6 Hz), 6.81 (1 H, s), 7.02, (1 H, s), 7.05 (1 H, d, J=7.7 Hz), 7.17 (2 H, m), 7.71 (1 H J=2.7 Hz), 9.72 (1 H, s), 10.60 (1 H, s); $^{13}$C NMR (75 MHz, DMSO-d$_6$)δ 74.37, 105.17, 116.48. 118.30, 122.34, 124.32, 125.92, 126.84, 128.33, 129.14, 129.26 (q), 136.87, 144.11, 152.37, 177.30; MS m/e 344 (MH$^+$).

Anal. calcd. for C$_{15}$H$_9$ClF$_3$NO$_3$: C, 52.42; H, 2.64; N, 4.08.

Found: C, 52.19; H, 2.57; N, 3.97.

Example 4

(±)-3-(5-Chloro-2-hydroxyphenyl)-1,3-dihydro-6-(trifluoromethyl)-2 H-indol-2-one A solution of BBr$_3$ (12 mL, 12 mmol; 1M in CH$_2$Cl$_2$) was added to a stirred cold (−78° C.) solution of (±)-3-(5-chloro-2-methoxyphenyl)-1,3-dihydro-6-(trifluoromethyl)-2H-indol-2-one (1.37 g, 4 mmol) in anhydrous CH$_2$Cl$_2$ (20 mL). The mixture was allowed to warm to ambient temperature and maintained for 2 hours. The reaction was quenched with saturated NaHCO$_3$ and then acidified with 1N HCl. The organic layer was separated, washed with water, brine and then dried (MgSO$_4$). Evaporation of CH$_2$Cl$_2$ gave an off-white solid which was triturated with warm CH$_2$Cl$_2$ to afford the title compound (1.21 g, 93%): mp 266°–268° C.; IR (KBr, cm$^{-1}$) 3320, 1690, 1310, 1250, 1160, 1125; $^1$H NMR (300 MHz, DMSO-d$_6$)δ 4.85 (1 H, s), 6.75 (1 H, d, J=8.6 Hz), 7.04 (1 H, s), 7.11, (1 H, d, J=7.7 Hz), 7.17 (1 H, dd, J=8.6 and 2.6 Hz), 7.22 (1 H, d, J=8.0 Hz), 7.26 (1 H, d, J=2.4 Hz), 9.82 (1 H, s), 10.73 (1 H, s); $^{13}$C NMR (75 MHz, DMSO-d$_6$)δ 48.47, 104.94, 116.84. 118.16, 122.27, 124.20, 125.61, 126.06, 128.05, 128.41, 130.76, 134.72, 143.69, 154.26, 176.92. MS m/e 328 (MH$^+$).

Anal. calcd. for C$_{15}$H$_9$ClF$_3$NO$_2$: C, 54.98; H, 2.77; N, 4.27.

Found: C, 54.84; H, 2.64; N, 4.16.

EXAMPLE 5

(±)-3-(5-Chloro-2-hydroxyphenyl)-1,3-dihydro-3-hydroxy-5-(trifluoromethyl)-2H-indol-2-one mp 156°–158° C.; IR (KBr, cm$^{-1}$) 3350, 1740, 1325, 1260, 1160, 1120; $^1$H NMR (300 MHz, DMSO-d$_6$)δ 6.62 (1 H, d, J=8.5 Hz), 6.80 (1 H, s), 6.98 (1 H, d, J=8.1 Hz), 7.09 (1 H, d, J=1.2 Hz), 7.17 (1 H, dd, J=8.5 and 2.7 Hz), 7.56 (1 H, dd, J=8.1 and 1.2 Hz), 7.73 (1 H, d, J=2.7 Hz), 9.73 (1 H, s), 10.72 (1 H, s); $^{13}$C NMR (75 MHz, DMSO-d$_6$)δ 74.37, 109.44, 116.52, 120.16, 121.75 (q), 122.37, 126.42, 126.75, 126.93, 128.37, 129.28, 133.33, 146.94, 152.36, 177.56; MS m/e 344 (MH$^+$).

Anal. calcd. for C$_{15}$H$_9$ClF$_3$NO$_3$: C, 52.42; H, 2.64; N, 4.08.

Found: C, 52.19; H, 2.48; N, 4.13.

EXAMPLE 6

(±)-3-(5-Chloro-2-hydroxyphenyl)-4,6-dichloro-1,3-dihydro-3-hydroxy-2-H-indol-2-one mp 232°–235° C. (dec.); IR (KBr, cm$^{-1}$) 3400, 1730, 1275; $^1$H NMR (300 MHz, DMSO-d$_6$)δ 6.61 (1 H, d, J=8.5 Hz), 6.79 (1 H, d, J=1.7 Hz), 6.81 (1 H, s), 6.94 (1 H, d, J=1.7 Hz), 7.14 (1 H, dd, J=8.5 and 2.7 Hz), 7.71 (1 H, d, J=2.7 Hz), 9.71 (1 H, s), 10.71 (1 H, s);$^{13}$C NMR (75 MHz, DMSO-d$_6$)δ 74.77, 108.31, 116.32, 121.22, 122.07, 127.55, 128.20, 128.39, 130.40, 134.05, 146.26, 152.27, 176.89; MS m/e 344 (MH$^+$).

Anal. calcd. for C$_{14}$H$_8$Cl$_3$NO$_3$: C, 48.80; H, 2.34; N, 4.06.

Found: C, 48.70; H, 2.35; N, 4.01.

EXAMPLE 7

(±)-3-(5-Chloro-2-hydroxyphenyl)-1,3-dihydro-3-hydroxy-7-(trifluoromethyl)-2H-indol-2-one mp 205°–207° C.; IR(KBr, cm$^{-1}$)3250, 1745, 1340, 1240, 1175, 1120; $^1$H NMR (300 MHz, DMSO-d$_6$)δ 6.59(1 H, d, J=8.5 Hz), 6.99(1 H, t, J=7.7 Hz), 7.10 (1 H, d, J=7.1 Hz), 7.16(1 H, dd, J=8.5 and 2.7 Hz), 7.44 (1 H, d, J=7.8 Hz), 7.72 (1 H, d, J=2.7 Hz), 9.79 (1 H, s), 10.79 (1 H, s); $^{13}$C NMR (75 MHz, DMSO-d$_6$)δ 73.41, 110.10 (q), 116.37, 121.43, 122.27, 125.16, 125.61, 126.83, 127.53, 128.30, 129.37, 134.40, 140.72, 152.38, 178.02; MS m/e 344(MH$^+$);

Anal. calcd. for C$_{15}$H$_9$ClF$_3$NO$_3$•0.2H$_2$O: C, 51.88; H, 2.73; N, 4.03.

Found: C, 51.87; H, 2.75; N, 3.98.

EXAMPLE 8

(±)-3-(5-Chloro-2-hydroxyphenyl)-1,3-dihydro-3-hydroxy-4-trifluoromethyl)-2H-indol-2-one mp 239°–242° C.; IR (KBr, cm$^{-1}$) 3300, 1725, 1330, 1250, 1170, 1140; $^1$H NMR (300 MHz, DMSO-d$_6$)δ 6.56 (1 H, d, J=8.5Hz), 6.76 (1 H, s), 7.07–7.13 (3 H, m), 7.39 (1 H, t, J=7.9 Hz), 7.66 (1 H, s), 9.57 (1 H, s), 10.71 (1 H, s); $^{13}$C NMR (75 MHz, DMSO-d$_6$)δ 74.93, 113.23, 116.01, 118.26, 121.60, 121.84, 125.50 (q), 127.77, 127.95, 128.76, 129.57, 129.73, 145.00, 152.40, 176.89; MS m/e 344 (MH$^+$).

Anal. calcd. for C$_{15}$H$_9$ClF$_3$NO3: C, 52.42; H, 2.64; N, 4.08.

Found: C, 52.16; H, 2.87; N, 4.06.

EXAMPLE 9

(±)-1,3-Dihydro-3-hydroxy-3-[2-hydroxy-5-(trifluoromethyl)phenyl]-6(trifluoromethyl)-2H-indol-2-one mp 175°–177° C.; $^1$H NMR (300 MHz, DMSO-d$_6$)δ 6.77 (1 H, d, J=8.3 Hz), 7.02–7.09 (2 H, m), 7.19 (1 H, d, J=7.7 Hz), 7.51 (1 H, d, J=8.3 Hz), 8.08 (1 H, s), 10.40 (1 H, s), 10.67 (1 H, s); MS m/e 378 (MH$^+$).

Anal. calcd. for C$_{16}$H$_9$F$_6$NO$_3$: C, 50.94; H, 2.40; N, 3.71.

Found: C, 50.85; H, 2.34; N, 3.76.

EXAMPLE 10

(±)-3-(5-Chloro-2-hydroxyphenyl)-1,3-dihydro-3-hydroxy-4,6-bis(trifluoromethyl)-2H-indol-2-one mp 191°–193° C.; IR (KBr, cm$^{-1}$) 3700–2500, 1740, 1280, 1170, 1130; $^1$H NMR (300 MHz, DMSO-d$_6$)δ 6.59 (1 H, d, J=8.5 Hz), 7.06 (1 H, s), 7.15 (1 H, dd, J=8.5 and 2.6 Hz), 7.34 (1 H, s), 7.45 (1 H, s) 7.68 (1 H, d, J=2.6 Hz), 9.74 (1 H, s), 11.07 (1 H, s); MS m/e 412 (MH$^+$).

Anal. calcd. for $C_{16}H_8ClF_6NO_3 \cdot 0.2H_2O$: C, 46.24; H, 2.05; N, 3.37.

Found: C, 46.24; H, 2.18; N, 3.27.

EXAMPLE 11

(–)-3-(5-Chloro-2-methoxyphenyl)-1,3-dihydro-3-hydroxy-6-(trifluoromethyl)-2H-indol-2-one Potassium bis(trimethylsilyl)amide solution (2.2 mL, 1.1 mmol, 0.5M in toluene) was added dropwise to a cold (–78° C.) stirred solution of (±)-3-(5-Chloro-2-methoxyphenyl)-1,3-dihydro-6-(trifluoromethyl)-2H-indol-2-one 342 mg, 1 mmol) in dry degased THF (3 mL) under argon. The resultant light yellow solution of the potassium enolate was stirred at –78° C. for 30 minutes. A solution of (1 S)-(+)-(10-camphorsulfonyl)oxaziridine (252 mg, 1.1 mmol) in dry degased THF (2 mL) was added dropwise over 5 minutes to the enolate solution at –78° C. The mixture was stirred at –78° C. for 1 hour and then allowed to warm in an ice-bath (0°–5° C.). The reaction was quenched with glacial AcOH (0.1 mL), diluted with ether (25 mL) followed by addition of a saturated NH$_4$Cl(10 mL) solution. Organic layer was separated, washed with saturated NaHCO$_3$, water, brine and then dried (Na$_2$SO$_4$). Filtration and evaporation of solvents gave 0.54 g of crude product which was triturated with ether to remove the insoluble, (camphorsulfonyl)imine by-product through filtration. Evaporation of the filtrate gave 0.39 g of product slightly contaminated with the by-product. The crude product (0.39 g) was triturated with boiling CH$_2$Cl$_2$ to afford 230 mg of pure desired hydroxyindalone. Concentration of the mother liquor followed by re-trituration with CH$_2$Cl$_2$ gave an additional 72 mg to afford 302 mg (84%) of combined product: mp 244°–245° C.; $[\alpha]_D^{25}$ –166.78° (CHCl$_3$); IR (KBr, cm$^{-1}$) 3300–3100, 1722, 1320, 1250, 1125; $^1$H NMR (300 MHz, DMSO-d$_6$)δ 3.42 (3 H, s), 6.90 (1 H, s), 6.93 (1 H, d, J=8.7 Hz), 7.04 (1 H, d, J=7.7 Hz), 7.05 (1 H, s), 7.19 (1 H, d, J=7.7 Hz), 7.35 (1 H, dd, J=8.7 and 2.7 Hz), 7.79 (1 H, d, J=2.7 Hz), 10.67 (1 H, brd s); MS m/e 358 (MH$^+$).

Anal. calcd. for $C_{16}H_{11}ClF_3NO_3$: C, 53.72; H, 3.10; N, 3.92.

Found: C, 53.77; H, 2.95; N, 3.95.

EXAMPLE 12

(+)-3-(5-Chloro-2-hydroxyphenyl)-1,3-dihydro-3.-hydroxy-6-(trifluoromethyl)-2H-indol-2-one A solution of BBr$_3$ (1.4 mL, 1M in CH$_2$Cl$_2$) was added dropwise to a cold (–78° C.) stirred solution of (–)-3-(5-chloro-2-methoxyphenyl)-1,3-dihydro-3-hydroxy-6-(trifluoromethyl)-2H-indol-2-one [prepared in Example 11] (170 mg, 0,475 mmol) in anhydrous CH$_2$Cl$_2$ (10 mL). The resultant mixture was warmed in an ice bath and maintained for 2 hours. The reaction was quenched with saturated NaHCO$_3$ and then acidified with 1N HCl. The cloudy organic layer was separated, rotary evaporated, redissolved in EtOAc (25 mL) and then combined with the aqueous layer. The EtOAc layer was separated and washed with water, brine and then dried (Na$_2$SO$_4$). Filtration and evaporation gave 198 mg of crude product which was flash chromatographed (silica gel/10% MeOH in CH$_2$Cl$_2$) to afford 164 mg (100%) of pure title compound as a white solid: mp 200°–201° C.; $[\alpha]_D^{25}$ +29.90° (CHCl$_3$); IR (KBr, cm$^{-1}$) 3540, 3350, 1725, 1320, 1160, 1130; $^1$H NMR (300 MHz, DMSO-d$_6$)δ 6.60 (1 H, d, J=8.5 Hz), 6.82 (1 H, brd s), 7.02, (1 H, s), 7.05 (1 H, d, J=7.6 Hz), 7.17 (2 H, m), 7.71(1 H, d, J=2.7 Hz), 9.75 (1 H, brd s), 10.61 (1 H, s); MS m/e 344 (MH$^+$).

Anal. calcd. for $C_{15}H_9ClF_3NO_3$: C, 52.42; H, 2.64; N, 4.08.

Found: C, 52.62; H, 2.48; N, 4.04.

EXAMPLE 13

(–)-3-(5-Chloro-2-hydroxyphenyl)-1,3-dihydro-3-hydroxy-6-(trifluoromethyl)-2H-indol-2-one mp 198°–200° C.; $[\alpha]_D^{25}$ –22.18° (CHCl$_3$); IR (KBr, cm$^{-1}$) 3540, 3300, 1725, 1320, 1125; $^1$H NMR (300 MHz, DMSO-d$_6$)δ 6.60 (1 H, d, J=8.6 Hz), 6.82 (1 H, brd s), 7.02, (1 H, s), 7.05 (1 H, d, J=7.6 Hz), 7.17 (2 H, m), 7.72 (1 H, d, J=2.7 Hz), 9.75 (1 H, brd s), 10.61 (1 H, s); MS m/e 344 (MH$^+$).

Anal. calcd. for $C_{15}H_9ClF_3NO_3$: C, 52.42; H, 2.64; N, 4.08.

Found: C, 52.40; H, 2.59; N, 4.01.

EXAMPLE 14

(–)-3-(5-Chloro-2-methoxyphenyl)-1,3-dihydro-3-fluoro-6-(trifluoromethyl)-2H-indol-2-one mp 168°–170° C.; IR (KBr, cm$^{-1}$) 3200, 1734, 1320, 1268, 1132; $^1$H NMR (300 MHz, CDCl$_3$)δ 3.53 (3 H, s), 6.76 (1 H, dd, J=8.7 and 1.0 Hz), 7.14 (1 H, d, J=2.0 Hz), 7.18 (1 H, dd, J=7.8 and 2.0 Hz), 7.26 (1 H, d, J=7.8 Hz), 7.33 (1 H, dd, J=8.7 and 2.6 Hz), 7.78 (1 H, dd, J=2.6 and 1.0 Hz), 9.00 (1 H, s). $^{19}$F NMR (282 MHz, CDCl$_3$)δ –63.10 (6-CF$_3$), –159.87 (3-F); MS m/e 360 (MH$^+$).

Anal. calcd. for $C_{16}H_{10}ClF_4NO_2$: C, 53.43; H, 2.80; N, 3.89.

Found: C, 53.44; H, 2.79; N, 3.84.

EXAMPLE 15

(±)-3-(5-Chloro-2-hydroxyphenyl)-1,3-dihydro-3-hydroxy-2H-benz[g]indol-2-one mp 170°–172° C.; $^1$H NMR (300 MHz, DMSO-d$_6$)δ 6.58 (1 H, d, J=8.5 Hz), 6.66 (1 H, s), 7.02 (1 H, d, J=8.2 Hz), 7.14 (1 H, dd, J=8.5 and 2.6 Hz), 7.42 (1 H, d, J=8.2 Hz), 7.45–7.53 (2 H, m), 7.76 (1 H, d, J=2.6 Hz), 7.85 (1 H, dd, J=7.2 and 2.1 Hz), 8.10 (1 H, d, J=7.2 Hz), 9.57 (1 H, brd s), 11.03 (1 H, s); MS m/e 324 [M-H]$^-$.

Anal. calcd. for $C_{18}H_{12}ClNO_3 \cdot 0.25H_2O$: C, 65.46; H, 3.82; N, 4.24.

Found: C, 65.48; H, 3.60; N, 3.89.

EXAMPLE 16

(±)-3-(5-Chloro-2-hydroxyphenyl)-1,3-dihydro-6-phenyl-2H-indol-2-one mp 221°–225° C. (dec.); $^1$H NMR (300 MHz, DMSO-$d_6$)δ 6.78 (1 H, J=9.1 Hz), 6.99 (1 H, d, J=7.6 Hz), 7.05 (1 H, d, J=6.6 Hz), 7.12–7.16 (3 H, m), 7.34 (1 H, t, J=7.3 Hz), 7.44 (2 H, t, J=7.2 Hz), 7.58 (2 H, d, J=7.6 Hz), 9.83 (1 H, s), 10.59 (1 H, s); MS m/e 336 (MH$^+$).

Anal. calcd. for $C_{20}H_{14}ClNO_2 \cdot H_2O$: C, 68.29; H, 4.01; N, 3.98.

Found: C, 68.47; H, 3.81; N, 3.89.

EXAMPLE 17

(±)-3-(5-Chloro-2-hydroxyphenyl)-1,3-dihydro-2H-benz[g]indol-2-one mp 211°–215° C. (dec.); $^1$H NMR (300 MHz, DMSO-$d_6$)δ 4.97 (1 H, s), 6.80 (1 H, d, J=8.9 Hz), 7.10–7.17 (3 H, s), 7.46–7.53 (3 H, m), 7.87 (1 H, d, J=7.5 Hz), 8.10 (1 H, d, J=8.0 Hz), 9.83 (1 H, s), 11.25 (1 H, s); MS m/e 308 [M-H]$^-$.

Anal. calcd. for $C_{18}H_{12}ClNO_2 \cdot H_2O$: C, 65.96; H, 4.31; N, 4.27.

Found: C, 65.87; H, 3.99; N, 3.88.

EXAMPLE 18

(±)-3-(5-Chloro-2-methoxyphenyl)-1,3-dihydro-3-fluoro-6-phenyl-2H-indol-2-one

IR (KBr, cm$^{-1}$) 3200, 1738, 1338, 1266, 1120, 766, 693; $^1$H NMR (300 MHz, CDCl$_3$)δ 3.56 (3 H, s), 6.76 (1 H, d, J=8.7 Hz), 7.11 (1 H, s), 7.14 (1 H J=2.3 Hz), 7.20 (1 H, d, J=7.9 Hz), 7.31 (1 H, dd, J=8.6 and 2.3 Hz), 7.37 (1 H, J=7.0 Hz), 7.43 (2 H, m), 7.54 (2 H, d, J=6.9 Hz), 7.80 (2 H, d, J=2.5 Hz); $^{19}$F NMR (282 MHz, CDCl$_3$)δ –156.62 (3-F); MS m/e 366 [M-H]$^-$.

EXAMPLE 19

(±)-3-(5-Chloro-2-methoxyphenyl)-1,3-dihydro-3-fluoro-6-iodo-2H-indol-2-one mp 205°–210° C.; IR (KBr, cm$^{-1}$) 3600–3200, 1736, 1266; $^1$H NMR (300 MHz, CDCl$_3$)δ 3.55 (3 H, s), 6.74 (1 H, d, J=9.8 Hz), 6.80 (1 H, dd, J=7.8 and 2.5 Hz), 7.26 (1 H, s), 7.28–7.35 (2 H, m), 7.66 (1 H, brd s), 7.74 (1 H, d, J=2.1 Hz); $^{19}$F NMR (282 MHz, CDCl$_3$)δ –28.75(?) (3-F); MS m/e 416 [M-H]$^-$.

EXAMPLE 20

(±)-3-(5-Chloro-2-hydroxyphenyl)-1,3-dihydro-6-(4-methylphenyl)-2H-indol-2-one mp 277°–279° C. (dec.); IR (KBr, cm$^{-1}$) 3200, 1686; $^1$H NMR (300 MHz, DMSO-$d_6$)δ 2.32 (3 H, s), 4.78 (1 H, s), 6.81 (1 H, d, J=9.1 Hz), 6.97 (1 H, d, J=7.7 Hz), 7.03 (1 H, d, J=9.1 Hz)), 7.09 (1 H, d, J=1.4 Hz), 7.12–7.16 (2 H, m), 7.24 (2 H, d, J=8.5 Hz), 7.47 (2 H, d, J=8.1 Hz), 9.87 (1 H, s), 10.58 (1 H, s); MS m/e 348 [(M-H)$^-$].

EXAMPLE 21

(±)-3-(5-Chloro-2-methoxyphenyl)-1,3-dihydro-3-fluoro-7-(trifluoromethyl)-2H-indol-2-one mp 230°–233° C.; IR (KBr, cm$^{-1}$) 3230, 1754, 1322, 1212, 1128; $^1$H NMR (300 MHz, CDCl$_3$)δ 3.52 (3 H, s), 6.73 (1 H, d, J=8.5 Hz), 7.08 (1 H, t, 8.1 Hz), 7.24 (1 H, s), 7.31 (1 H, dd, J=8.5 and 2.1 Hz), 7.51 (1 H, d, J=7.4 Hz), 7.62 (1 H, brd s), 7.76 (1 H, d, J=2.1 Hz); $^{19}$F NMR (282 MHz, CDCl$_3$) δ 61.03 (7-CF$_3$), –159.54 (3-F); MS m/e 358 [M-H]$^-$.

Anal. calcd. for $C_{16}H_{10}ClF_4NO_2$: C, 53.43; H, 2.80; N, 3.89.

Found: C, 53.09; H, 2.88; N, 3.78.

EXAMPLE 22

(±)-3-(5-Chloro-2-hydroxyphenyl)-1,3-dihydro-2H-benz[e]indol-2-one mp 158°–160° C.; $^1$H NMR (300 MHz, DMSO-$d_6$)δ 5.17 (1 H, brd s), 6.79 (1 H, brd s), 7.13 (1 H, d, J=6.5 Hz), 7.21–7.24 (3 H, m), 7.29–7.31 (2 H, m), 7.83 (3 H, m), 10.63 (1 H, s); MS m/e 308 [M-H]$^-$.

Anal. calcd. for $C_{18}H_{13}ClNO_2 \cdot 1.25H_2O$: C, 65.07; H, 4.40; N, 4.22.

Found: C, 64.70; H, 4.38; N, 4.08.

EXAMPLE 23

(±)-3-(5-Chloro-2-methoxyphenyl)-1,3-dihydro-3-fluoro-5-methyl-2H-indol-2-one mp 193°–195° C.; IR (KBr, cm$^{-1}$) 3200, 1732, 1270, 1216; $^1$H NMR (300 MHz, CDCl$_3$)δ 2.22 (3 H, s), 3.53 (3 H, s), 6.74 (1 H, d, J=8.4 Hz), 6.77 (1 H, d, J=7.5 Hz), 6.87 (1 H, s), 7.07 (1 H, d, J=8.0 Hz), 7.29 (1 H, dd, J=8.8 and 2.5 Hz), 7.77 (1 H, d, J=2.5 Hz), 8.16 (1 H, brd s); $^{19}$F NMR (282 MHz, CDCl$_3$)δ –157.38 (3-F); MS m/e 304 [M-H]$^-$.

Anal. calcd. for $C_{16}H_{13}ClFNO_2$: C, 62.86; H, 4.29; N, 4.58.

Found: C, 62.67; H, 4.29; N, 4.49.

EXAMPLE 24

(±)-3-(5-Chloro-2-methoxyphenyl)-1,3-dihydro-3-fluoro-4,6-bis-(trifluoromethyl)-2H-indol-2-one mp 262°–264° C.; IR (KBr, cm$^{-1}$) 3200, 1750, 1316, 1280, 1202, 1140; $^1$H NMR (300 MHz, CDCl$_3$)δ 3.38 (3 H, s), 6.63 (1 H, dd, J=8.7 and 1.1 Hz), 7.21 (1 H, dd, J=8.7 and 2.5 Hz), 7.29 (1 H, s), 7.33 (1 H, s), 7.63 (1H, d, J=2.1 Hz), 10.91 (1 H, brd s); $^{19}$F NMR (282 MHz, CDCl$_3$)δ –60.00 (CF$_3$), –63.40 (CF$_3$), –163.42 (3-F); MS m/e 426 [M-H]$^-$.

Anal. calcd. for $C_{17}H_9ClF_7NO_2$: C, 47.74; H, 2.12; N, 3.27.

Found: C, 47.58; H, 2.18; N, 3.19.

EXAMPLE 25

(±)-3-(5-Chloro-2-methoxyphenyl)-1,3-dihydro-3,5-difluoro-2H-indol-2-one mp 205°–207° C.; IR (KBr, cm$^{-1}$) 3200, 1732, 1272, 1218, 1144; $^1$H NMR (300 MHz, CDCl$_3$)δ 3.53 (3 H, s), 6.75 (1 H, dd, J=8.8 and 1.1 Hz), 6.78–6.84 (2 H, m), 6.95–7.02 (1 H, m), 7.31 (1 H, dd, J=8.7 and 2.6 Hz), 7.75

(1 H, d, J=2.1 Hz), 8.48 (1 H, brd s); $^{19}$F NMR (282 MHz, CDCl$_3$)δ −119.53 (5-F), −158.81 (3-F); MS m/e 308 [M-H]$^-$].

Anal. calcd. for C$_{15}$H$_{10}$ClF$_2$NO$_2$: C, 58.17; H, 3.25; N, 4.52.

Found: C, 58.02; H, 3.45; N, 4.41.

EXAMPLE 26

(±)-5-Bromo-3-(5-chloro-2-methoxyphenyl)-1,3-dihydro-3-fluoro-2H-indol-2one mp 206°–208° C.; IR (KBr, cm$^{-1}$) 3200, 1738, 1300, 1262, 1216, 1126, 820; $^1$H NMR (300 MHz, CDCl$_3$)δ 3.53 (3 H, s), 6.75 (1 H, d, J=8.2 Hz), 6.78 (1 H, d, J=7.4 Hz), 7.17 (1 H, s), 7.32 (1 H, dd, J=8.5 and 2.3 Hz), 7.41 (1 H, d, J=8.2 Hz), 7.74 (1 H, d, J=2.4 Hz), 8.37 (1 H, brd s); $^{19}$F NMR (282 MHz, CDCl$_3$)δ −158.55 (3-F); MS m/e 368 [M-H]$^-$].

Anal. calcd. for C$_{15}$H$_{10}$BrClFNO$_2$: C, 48.61; H, 2.72; N, 3.78.

Found: C, 48.71; H, 2.36; N, 3.58.

EXAMPLE 27

(±)-3-(5-Chloro-2-hydroxyphenyl)-1,3-dihydro-6-[4-(trifluoromethyl)phenyl]-2H-indol-2-one mp 221°–225° C.; IR (KBr, cm$^{-1}$) 3278, 1686, 1326, 1276; $^1$H NMR (300 MHz, DMSO-d$_6$)δ 4.81 (1 H, s), 6.77 (1 H, d, J=8.4 Hz), 7.04 (1 H, d, J=7.6 Hz), 7.10 (1 H, d, J=1.3 Hz), 7.14 (1 H, d, J=2.6 Hz), 7.18–7.23 (3 H, m), 7.77–7.84 (3 H, m), 9.83 (1 H, s), 10.64 (1 H, s); MS m/e 402 [M-H]$^-$].

Anal. calcd. for C$_{21}$H$_{13}$ClF$_3$NO$_2$•0.25H$_{20}$: C, 61.78; H, 3.33; N, 3.43.

Found: C, 61.97; H, 3.63; N, 3.62.

EXAMPLE 28

(±)-3-(5-Chloro-2-hydroxyphenyl)-1,3-dihydro-2H-indol-2-one mp 256°–258° C.; IR (KBr, cm$^{-1}$) 3300, 3200, 1680, 820, 750; $^1$H NMR (300 MHz, DMSO-d$_6$)δ 4.75 (1 H, s), 6.78 (1 H, d, J=8.6 Hz), 6.85 (2 H, t, J=8.1 Hz), 6.92 (1 H, d, J=7.2 Hz), 7.08 (1 H, d, J=2.5 Hz), 7.11–7.17 (2 H, m), 8.78 (1 H, s), 10.46 (1 H, s); $^{13}$C NMR (75 MHz, DMSO-d$_6$)δ 48.04, 109.09, 116.87, 121.31, 122.20, 123.72, 126.61, 127.64, 127.99, 130.01, 130.05, 142.78, 154.40, 177.17; MS m/e 260 (MH$^+$).

Anal. calcd. for C$_{14}$H$_{10}$ClNO$_2$: C, 64.75; H, 3.88; N, 5.39.

Found: C, 64.63; H, 3.93; N, 5.23.

EXAMPLE 29

(±)-3-(5-Chloro-2-methoxyphenyl)-1,3-dihydro-3-hydroxy-5-(trifluoromethyl)-2H-indol-2-one mp 218°–220° C.; IR (KBr, cm$^{-1}$) 3350, 1730, 1325, 1260, 1150, 1120; $^1$H NMR (300 MHz, DMSO-d$_6$)δ 3.41 (3 H, s), 6.88 (1 H, s), 6.93 (1 H, d, J=8.8 Hz), 7.01 (1 H, d, J=8.1 Hz), 7.09 (1 H, d, J=1.6 Hz), 7.35 (1 H, dd, J=8.7 and 2.7 Hz), 7.56 (1 H, dd, J=8.1 and 1.1 Hz), 7.80 (1 H, d, J=2.7 Hz), 10.77 (1 H, s); $^{13}$C NMR (75 MHz, DMSO-d$_6$)δ 55.97, 74.26, 109.51, 113.61, 120.06, 120.11, 121.8 (m, CF$_3$), 124.50, 126.37, 126.94, 128.72, 131.38, 133.10, 146.70, 154.31, 177.55; MS m/e 358 (MH$^+$).

Anal. calcd. for C$_{16}$H$_{11}$ClF$_3$NO$_3$: C, 53.72; H, 3.10; N, 3.92.

Found: C, 53.51; H, 3.00; N, 3.91.

EXAMPLE 30

(±)-5-Bromo-3-(5-chloro-2-methoxyphenyl)-1,3-dihydro-3-hydroxy-2H-indol-2-one mp 245°–247° C.; IR (KBr, cm$^{-1}$) 3450–3200, 1712, 1246; $^1$H NMR (300 MHz, DMSO-d$_6$)δ 3.42 (3 H, s), 6.79 (2 H, d, J=8.3 Hz), 6.91 (1 H, d, J=7.1 Hz), 6.93 (1 H, s), 7.31–7.36 (2 H, m), 7.76 (1 H, d, J=2.7 Hz), 10.50 (1 H, s); $^{13}$C NMR (75 MHz, DMSO-d$_6$)δ 5.95, 74.60, 111.25, 112.82, 113.49, 124.41, 126.25, 126.85, 128.59, 131.58, 131.68, 134.62, 142.34, 154.32, 177.12; MS m/e 370 (MH$^+$).

Anal. calcd. for C$_{15}$H$_{11}$BrClNO$_3$: C, 48.88; H, 3.01; N, 3.80.

Found: C, 49.52; H, 3.03; N, 3.58.

EXAMPLE 31

(±)-3-(5-Chloro-2-hydroxyphenyl)-4,6-dichloro-1,3-dihydro-2H-indol-2-one mp 238°–240° C.; IR (KBr, cm$^{-1}$) 3400, 1694, 1318; $^1$H NMR (300 MHz, DMSO-d$_6$)δ 4.83 (1 H, brd s), 6.70 (1 H, brd s), 6.82 (1 H, s), 7.01 (1 H, s), 7.14 (1 H, dd, J=8.7 and 2.4 Hz), 7.4 (1 H, brd s), 9.70 (1 H, brd s), 10.82 (1 H, s); MS m/e 328 (MH$^+$).

EXAMPLE 32

(±)-3-(5-Chloro-2-methoxyphenyl)-3-dibydro-3-hydroxy-6-iodo-2H-indol-2-one mp 209°–211° C.; $^1$H NMR (300 MHz, DMSO-d$_6$)δ 3.42 (3 H, s), 6.62 (1 H, d, J=7.7 Hz), 6.73 (1 H, s), 6.91 (1 H, d, J=8.8 Hz), 7.13 (1 H, d, J=1.4 Hz), 7.18 (1 H, dd, J=7.7 and 1.4 Hz), 7.32 (1 H, dd, J=8.8 and 2.7 Hz), 7.75 (1 H, d, J=2.7 Hz), 10.46 (1 H, s); $^{13}$C NMR (75 MHz, DMSO-d$_6$)δ 55.99, 74.34, 94.43, 113.48, 117.55, 124.36, 125.60, 126.76, 128.48, 129.99, 31.75, 132.06, 144.60, 154.33, 177.28; MS m/e 416 (MH$^+$).

Anal. calcd. for C$_{15}$H$_{11}$ClINO$_3$0.25CH$_2$Cl$_2$: C, 41.93; H, 2.65; N, 3.21.

Found: C, 41.98; H, 2.73; N, 3.19.

EXAMPLE 33

(±)-3-(5-Chloro-2-hydroxyphenyl)-1,3-dihydro-6-iodo-2H-indol-2-one mp 199°–203° C. (dec.); MS m/e 386 (MH$^+$).

Anal. calcd. for C$_{14}$H$_9$ClINO$_2$.H$_2$O: C, 39.04; H, 2.71; N, 3.14.

Found: C, 38.82; H, 2.40; N, 3.04.

EXAMPLE 34

(±)-3-(5-Chloro-2-methoxyphenyl)-1,3-dihydro-3-hydroxy-2H-benz[f]indol-2-one mp 305°–307° C. (dec.); IR (KBr, cm$^{-1}$) 3356, 1728, 1248; $^1$H NMR (300 MHz, DMSO-d$_6$)δ 3.32 (3 H, s), 6.79 (1 H, s), 6.89 (1 H, d, J=8.7 Hz), 7.14 (1 H, s), 7.24 (1 H, t, J=7.0 Hz), 7.32 (1 H, d, J=2.7 Hz), 7.35–7.41 (2 H, m), 7.75 (2 H, t, J=8.5 Hz), 7.85 (1 H, d, J=2.7 Hz), 10.71 (1 H, s); MS m/e 357 (M+NH$_4$)$^+$.

EXAMPLE 35

(±)-3-(5-Chloro-2-hydroxyphenyl)-1,3-dihydro-3-hydroxy-2 H-benz[f]indol-2-one mp 160°–165° C. (dec.); IR (KBr, cm$^{-1}$) 3400, 1706; $^1$H NMR (300 MHz, CDCl$_3$–CD$_3$OD)δ 6.71 (1 H, dd, J=7.4 and 1.4 Hz), 7.03 (1 H, s), 7.05 (1 H, d, J=2.6 Hz), 7.12 (1 H, s), 7.22 (2 H, m), 7.29 (1 H, d, J=8.1 Hz), 7.38 (2 H, t, J=8.2 Hz), 7.64–7.69 (3 H, m); MS m/e 324 (M-H)$^-$.

EXAMPLE 36

(±)-3-(5-Chloro-2-hydroxyphenyl)-1,3-dihydro-2 H-benz[f]indol-2-one mp 254°–256° C. (dec.); IR (KBr, cm$^{-1}$) 3300, 1690, 1250, 740; $^1$H NMR (300 MHz, DMSO-d$_6$)δ 4.88 (1 H, s), 6.75 (1 H, d, J=8.6 Hz), 7.15 (1 H, s), 7.18 (1 H, d, J=2.7 Hz), 7.22–7.27 (2 H, m), 7.37 (1 H, t, J=8.1 Hz), 7.42 (1 H, s), 7.55 (2 H, t, J=9.4 Hz), 9.75 (1 H, s), 10.77 (1 H, s); MS m/e 308 (M-H)$^-$.

EXAMPLE 37

(3S)-(+)-(5-Chloro-2-methoxyphenyl)-1,3-dihydro-3-fluoro-6-(trifluoromethyl)-2H-indol-2-one The racemic compound of Example 14 was separated into its enantiomers using a Chiracel-OD analytical HPLC column (250×4.6 mm) using 9:1 hexanes/isopropyl alcohol as the eluting solvent at a flow rate of 0.75 mL/min. The detection method employed a HP 1090 UV detector with diode array at a wavelength of 220 nm. The first enantiomer which eluted from the column had a retention time of about 8.22 minutes and was determined to be the (+)-enantiomer of the title compound. On a preparative scale, up to one gram of the racemate may be resolved with a single injection on a 5×50 cm Chiracel-OD preparative HPLC column using 9:1 hexanes/isopropyl alcohol at a flow rate of 85 mL/min with baseline separation. Recrystallization of the enantiomer from methylene chloride/ hexanes provided crystals suitable for single crystal X-ray analysis. Using the anomalous scattering from the chlorine atom, the absolute configuration at the asymmetric carbon atom was established as S for the (+)-enantiomer. The enantiomer was identical to the racemate with respect to NMR, mass spectra, TLC and IR. The title compound was found to have a mp=198°–200° C. and $[\alpha]_D^{25}$+149.84° (MeOH).

EXAMPLE 38

(3R)-(-)-(5-Chloro-2-methoxyphenyl)-1,3-dihydro-3-fluoro-6-(trifluoromethyl)-2H-indol-2-one The racemic compound of Example 14 was separated into its enantiomers using a Chiracel-OD analytical HPLC column (250×4.6 mm) using 9:1 hexanes/isopropyl alchohol as the eluting solvent at a flow rate of 0.75 mL/min. The detection method employed a HP 1090 UV detector with diode array at a wavelength of 220 nm.

From the experimental process described in Example 37, the second enantiomer eluted from the same column at a retention time of about 11.58 minutes and was determined to be the (-)-enantiomer of the title compound. On a preparative scale, up to one gram of the racemate may be resolved with a single injection on a 5×50 cm Chiracel-OD preparative HPLC column using 9:1 hexanes/isopropyl alcohol at a flow rate of 85 mL/min with baseline separation. Recrystallization of the individual enantiomer from methylene chloride/hexanes provided crystals suitable for single crystal X-ray analysis. Using the anomalous scattering from the chlorine atom, the absolute configuration at the asymmetric carbon atom was established as R for the (-)-enantiomer. The enantiomer was identical to the racemate with respect to NMR, mass spectra, TLC and IR. The title compound was found to have a mp=199°–201° C. and $[\alpha]_D^{25}$-149.43°(MeOH).

What is claimed is:

1. A compound which is (3S)-(+)-(5-chloro-2-methoxyphenyl)-1,3-dihydro-3-fluoro-6-(trifluoromethyl)-2H-indol-2-one.

2. A compound which is (3R)-(-)-(5-chloro-2-methoxyphenyl)-1,3-dihydro-3-fluoro-6-(trifluoromethyl)-2H-indol-2-one.

3. A pharmaceutical composition for the treatment of disorders responsive to openers of the large conductance calcium-activated potassium channels comprising a therapeutically effective amount of the compound of claim 1 in association with a pharmaceutically acceptable carrier or diluent.

4. A pharmaceutical composition for the treatment of disorders responsive to openers of the large conductance calcium-activated potassium channels comprising a therapeutically effective amount of the compound of claim 2 in association with a pharmaceutically acceptable carrier or diluent.

5. A method for the treatment of disorders responsive to opening of the large conductance calcium-activated potassium channels in a mammal in need thereof, which comprises administering to said mammal a therapeutically effective amount of the compound of claim 1.

6. A method for the treatment of disorders responsive to opening of the large conductance calcium-activated potassium channels in a mammal in need thereof, which comprises administering to said mammal a therapeutically effective amount of the compound of claim 2.

7. A method of claim 5 wherein said disorder is ischemia, convulsions, asthma, urinary incontinence and traumatic brain injury.

8. A method of claim 5 wherein said disorder is cerebral ischemia.

9. A method of claim 6 wherein said disorder is ischemia, convulsions, asthma, urinary incontinence and traumatic brain injury.

10. A method of claim 6 wherein said disorder is cerebral ischemia.

\* \* \* \* \*

UNITED STATES PATENT AND TRADEMARK OFFICE
CERTIFICATE OF CORRECTION

PATENT NO: 5,602,169

DATED: February 11, 1997

INVENTOR(S): Piyasena Hewawasam, Nicholas A. Meanwell and Valentin K. Gribkoff It is certified that error appears in the above-identified patent and that said Letters Patent is hereby corrected as shown below:

column 26, lines 39 - 40, should read (±)-3-(5-Chloro-2-methoxyphenyl)-1,3-dihydro-3-fluoro-6-(trifluoromethyl)-2*H*-indol-2-one Signed and Sealed this Twentieth Day of May, 1997

*Attest:*

BRUCE LEHMAN

*Attesting Officer*   *Commissioner of Patents and Trademarks*